(12) United States Patent
Lohray et al.

(10) Patent No.: US 6,608,194 B1
(45) Date of Patent: Aug. 19, 2003

(54) TRICYCLIC COMPOUNDS AND THEIR USE IN MEDICINE; PROCESS FOR THEIR PREPARATION AND PHARMACEUTICAL COMPOSITIONS CONTAINING THEM

(75) Inventors: Braj Bhushan Lohray, Hyderabad (IN); Vidya Bhushan Lohray, Hyderabad (IN); Ashok Channaveerappa Bajji, Salt Lake City, UT (US); Shivaramayya Kalchar, Taipei (TW); Rao Bheema Paraselli, Hyderabad (IN); Ranga Madhavan Gurram, Hyderabad (IN)

(73) Assignee: Dr. Reddy's Laboratories Limited, Hyderabad (IN)

( * ) Notice: Subject to any disclaimer, the term of this patent is extended or adjusted under 35 U.S.C. 154(b) by 0 days.

(21) Appl. No.: 09/853,177

(22) Filed: May 10, 2001

(Under 37 CFR 1.47)

Related U.S. Application Data

(60) Division of application No. 09/257,104, filed on Feb. 24, 1999, now Pat. No. 6,440,961, which is a continuation-in-part of application No. 09/012,585, filed on Jan. 23, 1998, now Pat. No. 6,054,453.

(30) Foreign Application Priority Data

Oct. 27, 1997 (IN) ........................ 2416/MAS/97

(51) Int. Cl.$^7$ ..................... C07D 265/38; C07D 279/22
(52) U.S. Cl. ............. 544/34; 544/38; 544/42; 544/43; 544/46; 544/101; 544/102; 544/345; 544/347
(58) Field of Search ............ 514/224.5, 225.2, 514/225.8, 226.2, 229.8, 250; 544/34, 38, 42, 43, 46, 101, 102, 345, 347

(56) References Cited

U.S. PATENT DOCUMENTS

| | | | |
|---|---|---|---|
| 5,104,888 A | 4/1992 | Yoshioka | 514/369 |
| 5,227,490 A | 7/1993 | Hartman | 514/317 |
| 5,306,726 A | 4/1994 | Hulin | 514/375 |
| 5,648,368 A | 7/1997 | Egbertson | 514/317 |
| 5,801,173 A | 9/1998 | Lohray et al. | 514/252 |
| 5,885,997 A | 3/1999 | Lohray et al. | 514/256 |
| 5,889,025 A | 3/1999 | Lohray et al. | 514/326 |
| 5,889,032 A | 3/1999 | Lohray et al. | 514/369 |
| 5,919,782 A | 7/1999 | Lohray et al. | 514/252 |
| 5,925,656 A | 7/1999 | Kallam et al. | 514/369 |
| 5,985,884 A | 11/1999 | Lohray et al. | 514/259 |
| 6,011,031 A | 1/2000 | Lohray et al. | 514/224.2 |
| 6,011,036 A | 1/2000 | Lohray et al. | 514/248 |
| 6,030,973 A | 2/2000 | Lohray et al. | 514/259 |
| 6,054,453 A | 4/2000 | Lohray et al. | 514/226.2 |
| 6,130,214 A | 10/2000 | Lohray et al. | 514/224.2 |
| 6,159,966 A | 12/2000 | Lohray et al. | 514/224.8 |

FOREIGN PATENT DOCUMENTS

| | | |
|---|---|---|
| EP | 0441539 | 8/1991 |
| WO | 9119702 | 12/1991 |
| WO | 9401420 | 1/1994 |
| WO | 9413650 | 6/1994 |
| WO | 9517394 | 6/1995 |
| WO | 9604260 | 2/1996 |
| WO | 9725042 | 7/1997 |
| WO | 9741097 | 11/1997 |
| WO | 0140159 | 6/2001 |
| WO | 0140165 | 6/2001 |
| WO | 0140166 | 6/2001 |
| WO | 0140169 | 6/2001 |
| WO | 0140170 | 6/2001 |
| WO | 0140171 | 6/2001 |
| WO | 0140172 | 6/2001 |
| WO | 0153257 | 7/2001 |

OTHER PUBLICATIONS

Buckle, D.R. "Non Thiazolidinedione Antihyperglyceaemic Agents..." Bioorganic & Medicinal Chemistry Letters, vol. 6, No. 17, pp. 2121–2126, 1996.

Hulin, B. "Hypoglycemic Activity of a Series of . . . " J. Med. Chem. 36, 1996, pp. 3897–3907.

Patent Abstracts of Japan vol. 97, No. 5, May 30, 1997 & JP 09 012575, Jan. 14, 1997.

*Primary Examiner*—Richard L. Raymond
(74) *Attorney, Agent, or Firm*—Ladas & Parry

(57) ABSTRACT

A compound of Formula (Ih)

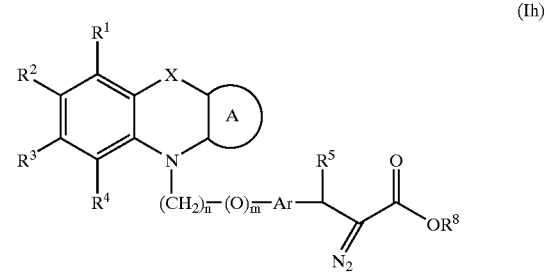

The compounds may be used, inter alia, for preparing beta aryl-alpha-oxy substituted alkylcarboxylic acids.

8 Claims, No Drawings

TRICYCLIC COMPOUNDS AND THEIR USE IN MEDICINE; PROCESS FOR THEIR PREPARATION AND PHARMACEUTICAL COMPOSITIONS CONTAINING THEM

This application is a divisional of application Ser. No. 09/257,104, filed Feb. 24, 1999, now U.S. Pat. No. 6,440, 961, which in turn is a continuation-in-part of application Ser. No. 09/012,585, filed Jan. 23, 1998, now U.S. Pat. No. 6,054,453.

FIELD OF THE INVENTION

The present invention relates to novel hypolipidemic, antihyperglycemic, antiobesity and hypocholesterolemic compounds, their derivatives, their analogs, their tautomeric forms their stereoisomers, their polymorphs, their pharmaceutically acceptable salts, their pharmaceutically acceptable solvates and pharmaceutically acceptable compositions containing these. More particularly, the present invention relates to novel β-aryl-α-oxysubstituted alkylcarboxylic acids of the general formula (I), their derivatives, their analogs. Their tautomeric forms, their stereoisomers, their polymorphs, their pharmaceutically acceptable salts, their pharmaceutically acceptable solvates and pharmaceutically compositions containing them.

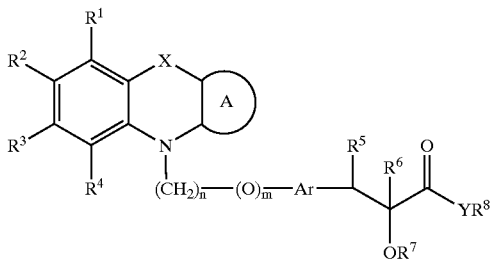

(I)

The present invention also relates to a process for the preparation of the above said novel compounds, their analogs, their derivatives, their tautomeric forms, their stereoisomers, their polymorphs, their pharmaceutically acceptable salts, pharmaceutically acceptable solvates and pharmaceutical compositions containing them.

The present invention also relates to novel intermediates, processes for their preparation and their use in the preparation of compounds of formula (I).

The compounds of the present invention lower plasma glucose, triglycerides, total cholesterol (TC); increase high density lipoprotein (HDL) and decrease low density lipoprotein (LDL), which have beneficial effects on coronary heart disease and atherosclerosis.

The compounds of general formula (I) are useful in reducing body weight and for the treatment and/or prophylaxis of diseases such as hypertension, coronary heart disease, atherosclerosis, stroke, peripheral vascular diseases and related disorders. These compounds are useful for the treatment of familial hypercholesterolemia, hypertriglycaridemia, lowering of atherogenic lipoproteins, VLDL and LDL. The compounds of the present invention can be used for the treatment of certain renal diseases including glomerulonephritis, glomerulosclerosis, nephrotic syndrome, hypertensive nephrosclerosis, retinopathy and nephropathy. The compounds of general formula (I) are also useful for the treatment and/or prophylaxis of insulin resistance (type II diabetes), leptin resistance, impaired glucose tolerance, dyslipidemia and disorders related to syndrome X such as hypertension, obesity, insulin resistance, coronary heart disease, and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, xanthoma, inflammation and for the treatment of cancer. The compounds of the present inventions are useful in the treatment and/or prophylaxis of the above said diseases is combination/concomitant with one or more HMG CoA reductase inhibitors, hypolipidemic/hypolipoproteinemic agents such as fibric acid derivatives, nicotinic acid, cholestyramine, colestipol, probucol.

BACKGROUND OF INVENTION

Atherosclerosis and other peripheral vascular diseases are the major causes affecting the quality of life of millions of people. Therefore, considerable attention has been directed towards understanding the etiology of hypercholesterolemia and hyperlipidemia and development of effective therapeutic strategies.

Hypercholesterolemia has been defined as plasma cholesterol level that exceeds an arbitrarily defined value called "normal" level. Recently, it has been accepted that "ideal" plasma levels of cholesterol are much below the "normal" level of cholesterol in general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol in present in the esterified forms with various lipoproteins such as Low density lipoprotein (LDL), Intermediate density lipoprotein (IDL), High density lipoprotein (HDL) and partially as Very low density lipoprotein (VLDL). Studies clearly indicate that there is an inverse correlationship between CAD and atherosclerosis with serum HDL-cholesterol concentrations. (Stampfer et al., *N. Engl. J. Med.*, 325 (1991), 373–381) and the risk of CAD increases with increasing levels of LDL and VLDL.

In CAD, generally "fatty streaks" in carotid, coronary and cerebral arteries, are found which are primarily free and esterified cholesterol. Miller et al., (*Br. Med. J.*, 282 (1981), 1741–1744) have shown that increase is HDL-particles may decrease the number of sites of stenosis in coronary arteries of human, and high level of HDL-cholesterol may protect against the progression of atherosclerosis. Picardo et al., (*Arteriosclerosis* 6 (1986) 434–441) have shown by in vitro experiment that HDL in capable of removing cholesterol from cells. They suggest that HDL may deplete tissues of excess free cholesterol and transfer it to the liver (MaciKinnon et al., *J. Biol. Chem.* 261 (1986), 2548–2552). Therefore, agents that increase HDL cholesterol would have therapeutic significance for the treatment of hypercholesterolemia and coronary heart diseases (CHD).

Obesity is a disease highly prevalent is affluent societies and in the developing world and is a major cause of morbidity and mortality. It is a state of excess body fat accumulation. The causes of obesity are unclear. It in believed to be of genetic origin or promoted by an interaction between the genotype and environment. Irrespective of the cause, the, result is fat deposition due to imbalance between the energy intake versus energy expenditure.

Dieting, exercise and appetite suppression have been a part of obesity treatment. There is a need for efficient therapy to fight this disease since it may lead to coronary heart disease, diabetes, stroke, hyperlipidemia, gout, osteoarthritis, reduced fertility and many other psychological and social problems.

Diabetes and insulin resistance is yet another disease which severely effects the quality of life of a large population in the world. Insulin resistance in the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and in associated with a variety of abnormalities including obesity, hypertension, hyperlipidemia (J. Clin. Invest, (1985) 75: 809–817; N. Engl. J. Med. (1987) 317: 350–357; J. Clin Endocrinol. Metab., (1988) 66: 580–583; J. Clin. Invest., (1975) 68: 957–969) and other rural complications (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as syndrome having insulin resistance as the central pathogenic link-Syndrome-X.

Hyperlipidemia is the primary cause for cardiovascular (CVD) and other peripheral vascular diseases. High risk of CVD is related to the higher LDL (Low Density Lipoprotein) and VLDL (Very Low Density Lipoprotein seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help is preventing cardiovascular diseases.

Peroxisome proliferator activated receptors (PPAR) ere members of the nuclear receptor super family. The gamma ($\gamma$) isoform of PPAR (PPAR$\gamma$) has been implicated in regulating differentiation of adipocytes (Endocrinology, (1994) 135: 798–800) and energy homeostasis (Cell, (1995) 83: 803–812), whereas the alpha ($\alpha$) isoform of PPAR (PPAR$\alpha$) mediates fatty acid oxidation (Trend Endocrin. Metab., (1993) 4 : 291–296) thereby resulting in reduction of circulating free fatty acid in plasma (Current Biol. (1995) is: 618–621). PPAR$\alpha$ agonists have been found useful for the treatment of obesity (WO 97/36579). It has been recently disclosed that the hypolipidemic effect is enhanced when a molecule has both PPAR$\alpha$ and PPAR$\gamma$ agonism activity and suggested to be useful for the treatment syndrome X (WO 91/25042). Synergism between the insulin sensitizer PPAR$\gamma$ agonist) and HMG CoA reductase inhibitor has been observed which is useful for the treatment of atherosclerosis and xanthoma. (EP 0 753 298).

It is known that PPAR$\gamma$ plays an important role in adipocyte differentiation (Cell. (1996) 87, 377–389). Ligand activation of PPAR is sufficient to cause complete terminal differentiation (Cell, (1994) 79,1147–1156) including cell cycle withdrawal. PPAR$\gamma$ is consistently expressed in certain cells and activation of this nuclear receptor with PPAR$\gamma$ agonists would stimulate the terminal differentiation of adipocyte precursors and cause morphological and molecular changes characteristics of a more differentiated less malignant state (Molecular Cell, (1998), 465–470; Carcinogenesis, (1998), 1949–53; Proc. Natl. Acad. Sci., (1997) 94, 237–241) and inhibition of expression of prostate cancer tissue (Cancer Research (1998), 58; 3344–3352). This would be useful in the treatment of certain types of cancer, which express PPAR$\gamma$ and could lead to a quite nontoxic chemotherapy.

Leptin resistance is a condition wherein the target cells are unable to respond to leptin signal. This may give rise to obesity due to excess food intake and reduced energy expenditure and cause impaired glucose tolerance, type 2 diabetes, cardiovascular diseases and such other interrelated complications. Kallen et al (Proc. Natl. Acad. Sci., (1996) 93, 5793–5796) have reported that insulin sensitizers which perhaps due to their PPAR agonist expression and lower plasma leptin concentration. However, it has been recently disclosed that compounds having insulin sensitizing property also possess leptin sensitization activity. They lower the circulating plasma leptin concentrations by improving the target cell response to leptin (WO 93/02159).

A few $\beta$-aryl-$\alpha$-hydroxy propionic acids, their derivatives and their analogs have been reported to be useful in the treatment of hyperglycemia, hyperlipidemia and hypercholesterolemia. Some of such compounds described in the prior art are outlined below i) U.S. Pat. No. 5,306,726; WO 91/19702 disclose several 3-aryl-2-hydroxypropionic acid derivatives of general formula (IIa) and (IIb) as hypolipidemic and hypoglycemic agents.

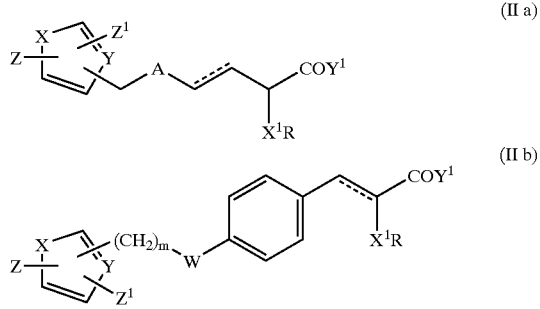

Examples of these compounds are shown in formula (IIc) and (IId)

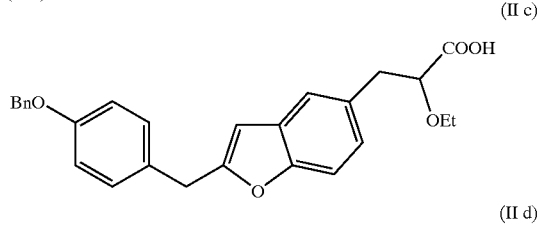

ii) International Patent Applications, WO 95/03038 and WO 96/04260 disclose compounds of formula (IIe)

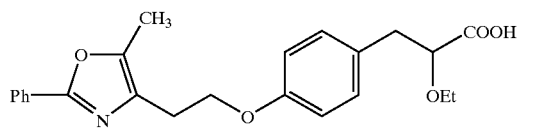

wherein $R^a$ represents 2-benzoxazolyl or 2-pyridyl and $R^b$ represent $CF_3$, $CH_2OCH_3$ or $CH_3$. A typical example in (S)-3-[4-[2-[N-(2-benzoxazoly]-N-methylamino]ethoxy]phenyl]-2-(2,2,2-trifluoroethoxy)propanoic acid (IIf).

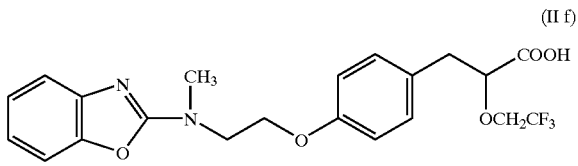

(II f)

iii) International Patent Application Nos. WO 94/13650, WO 94/01420 and WO 95/17394 disclose the compounds of general formula (IIg)

(IIg)

wherein $A^1$ represent aromatic heterocycle, $A^2$ represents substituted benzene ring and $A^3$ represents moiety of formula $(CH_2)_m$—CH—$(OR^1)$, wherein $R^1$ represents alkyl groups m is an integer of 1 to 5; X represents substituted or unsubstituted N; Y represents C=O or C=S. $R^2$ represents $OR^3$ where $R^3$ in alkyl, aralkyl or aryl group and a in integer is the range of 2–6. An example of these compounds is shown is formula (IIh)

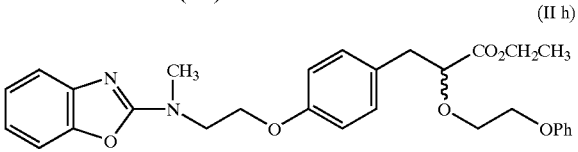

(II h)

SUMMARY OF THE INVENTION

With an objective to develop novel compounds for the treatment and/or prophylaxis of diseases related to increased levels of lipids, atherosclerosis, coronary artery diseases especially to treat hypertriglyceridemia and to lower free fatty acids, for the treatment and/or prophylaxis of diseases described as Syndrome-X which include hyperlipidemia, hyperinsulinemia, obesity, insulin resistance, insulin resistance leading to type 2 diabetes acid diabetes complications thereof, for the treatment of diseases wherein insulin resistance in the pathophysiological mechanism, for the treatment of hypertension, atherosclerosis and coronary artery diseases with better efficacy, potency and lower toxicity, we focused our research to develop new compounds effective in the treatment of above mentioned diseases. Effort in this direction has led to compounds having general formula (I).

The main objective of the present invention is therefore, to provide novel β-aryl-α-oxysubstituted alkylcarboxylic acids and their derivatives, their analogs, their tautomeric forms, their stereoisomers, their polymorphs, their pharmaceutically acceptable salts, their pharmaceutically acceptable solvates and pharmaceutical compositions containing them, or their mixtures.

Another objective of the present invention is to provide novel β-aryl-α-oxysubstituted alkylcarboxylic acids and their derivatives, their analogs, their tautomeric forms, their stereoisomers, their polymorphs, their pharmaceutically acceptable salts, their pharmaceutically acceptable solvates and pharmaceutical compositions containing them or their mixtures which may have agonist activity against PPARα and/or PPARγ and optionally inhibit HMG CoA reductase, is addition to agonist activity against PPARα and/or PPARγ.

Another objective of the present invention is to provide novel β-aryl-α-oxysubstituted alkylcarboxylic -acids and their derivatives, their analogs their tautomeric forms, their stereoisomers, their polymorphs, their pharmaceutically acceptable salts, their pharmaceutically acceptable solvates and pharmaceutical compositions containing them or their mixtures having enhanced activities, without toxic effect or with, reduced toxic effect.

Yet another objective of the present invention is to produce a process for the preparation of novel β-aryl-α-oxysubstituted alkylcarboxylic acids and them derivatives of the formula (I) as defined above, their analogs, their tautomeric forms, their stereoisomers, their polymorphs, their pharmaceutically acceptable salts and their pharmaceutically acceptable solvates.

Still another objective of the present invention is to provide pharmaceutical compositions containing compounds of the general formula (I), their analogs, their derivatives, their tautomers, their stereoisomers, their polymorphs, their salts, solvates or them mixtures in combination with suitable carriers, solvents, diluents and other media normally employed in preparing such compositions.

DETAILED DESCRIPTION OF THE INVENTION

The present invention is related to compounds having the general formula (I)

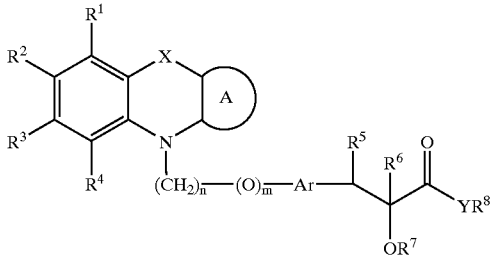

(I)

where $R^1$, $R^2$, $R^3$, $R^4$ are same or different and represent hydrogen, halogen, hydroxy, nitro, cyano, formyl or unsubstituted or substituted groups selected from alkyl, cycloalkyl, alkoxy. cycloalkoxy, aryl, aryloxy, aralkyl, aralkoxy, heterocyclyl, aryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, acid or its derivatives, or sulfonic acid or its derivatives; the ring A fused to the ring containing X and N represents a 5–6 membered cyclic structure containing carbon atoms, which may optionally contain one or more heteroatoms selected from oxygen, sulfur or nitrogen atoms, which may optionally be substituted; the ring A may be saturated or contain one or more double bonds or may be aromatic; X represents a heteroatom selected from oxygen, sulfur or $NR^9$ where $R^9$ is hydrogen, alkyl, aryl, alkyl, acyl, alkoxycarbonyl, aryloxycarbonyl or aralkoxycarbonyl; Ar represents an unsubstituted of substituted divalent single or fused aromatic or heterocyclic group; RS represents hydrogen atom, hydroxy, alkoxy, halogen, lower alkyl or unsubstituted or substituted aralkyl group or forms a bond together with the adjacent group $R^6$; $R^6$ represents hydrogen, hydroxy, alkoxy, halogen, lower alkyl group, acyl or unsubstituted or substituted aralkyl or $R^6$ forms a bond together with $R^5$; $R^7$ represents hydrogen or unsubstituted or substituted groups selected from alkyl, cycloalkyl, aryl, aralkyl, alkoxyalkyl, alkoxycarbonyl, aryloxycarbonyl alkylaminocarbonyl, arylaminocarbonyl, acyl, heterocyclyl, heteroaryl or heteroaralkyl groups; $R^8$ represents hydrogen or unsubstituted or substituted groups selected from alkyl, cycloalkyl, aryl, aralkyl, heterocyclyl, heteroaryl or heteroaralkyl groups; Y represents oxygen or $NR^{10}$, where $R^{10}$ represents hydrogen, alkyl, aryl, hydroxyalkyl, aralkyl, heterocylcyl, heteroaryl or heteroaralkyl groups; $R^8$ and $R^{10}$ together may form a 5 or 6 membered cyclic structure containing carbon atoms, which may optionally contain one or more heteroatoms selected from oxygen, sulfur or nitrogen; n is an integer ranging from 1–4 and m is an integer 0 or 1.

Suitable groups represented by $R^1$–$R^4$ include hydrogen, halogen atom such as fluorine, chlorine, bromine, or iodine; hydroxy, cyano, nitro, formyl; substituted or unsubstituted $(C_1$–$C_{12})$alkyl group, especially, linear or branched $(C_1$–$C_6)$ alkyl group such as methyl, ethyl, n-propyl, isopropyl, n-butyl, iso-butyl, t-butyl, n-pentyl, isopentyl, hexyl and the like; cyclo $(C_3$–$C_6)$alkyl group such as cyclopropyl, cyclobutyl, cyclopentyl, cyclohexyl and the like, the cycloalkyl group may be substituted; cyclo$(C_3$–$C_6)$alkoxy group such as cyclopropyloxy, cyclobutyloxy, cyclopentyloxy, cyclohexyloxy and the like, the cycloalkoxy group may be substituted; aryl group such as phenyl, naphthyl and the like, the aryl getup may be substituted; aralkyl such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heterocyclyl groups such as azidinyl, pyrrolidinyl, morpholinyl, piperidinyl, piperazinyl and the like, the heterocyclyl group may be substituted; aralkoxy group such as (I), benzyloxy, phenethyloxy, naphthylamethyloxy, phenylpropyloxy and the like, the aralkoxy getup may be substituted; heteroaralkyl group such as furanmethyl, pyridinemethyl, oxazolemethyl, oxazolethyl and the like, the heteroaralkyl group may be substituted; aralkylamino group such as $C_6H_5CH_2NH$, $C_6H_5CH_2CH_2NH$, $C_6H_5CH_2NCH_3$ and the like, which may be substituted; alkoxycarbonyl such as methoxycarbonyl, ethoxycarbonyl and the like, the alkoxycarbonyl group may substituted; aryloxycarbonyl group such as substituted or unsubstituted phenoxycarbonyl, naphthyloxycarbonyl and the like, the aryloxycarbonyl group may be substituted; aralkoxycarbonyl group such as benzyloxycarbonyl, phenethyloxycarbonyl, naphthylmethoxycarbonyl and the like, which may be substituted; monoalkylamino group such as $NNCH_3$, $NHC_2H_5$, $NHC_3H_7$, $NHC_6H_{13}$ and the like, which may be substituted; dialkylamino group such as $N(CH_3)_2$, $NCH_3(C_2H_5)$ and the like, which may be substituted; alkoxyalkyl group such as methoxymethyl, ethoxymethyl, methoxyethyl, ethoxyethyl and the like, the alkoxyalkyl group may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; heteroaryloxy and heteroaralkoxy, wherein heteroaryl and heteroaralkyl moieties are as defined earlier and may be substituted; aryloxy group such as phenoxy, naphthyloxy and the like, the aryloxy group may be substituted; arylamino group such as $HNC_6H_5$, $NCH_3(C_6H_5)$, $NHC_6H_4CH_3$, $NHC_6H_4$-Hal and the like, the arylamino group may be substituted amino, group; amino $(C_1$–$C_6)$alkyl, which may be substituted; hydroxy$(C_1$–$C_6)$alkyl, which may be substituted; $(C_1$–$C_6)$ alkoxy such as methoxy, ethoxy, propyloxy, butyloxy, isopropyloxy and the like, which may be substituted; thio $(C_1$–$C_6)$alkyl, which may be substituted; $(C_1$–$C_6)$alkylthio, which may be substituted; acyl group such as acetyl, propionyl, benzoyl and the like, the acyl group may be substituted; acylamino groups such as $NHCOCH_3$, $NHCOC_2H_5$, $NHCOC_3H_7$, $NHCOC_6H_5$ and the like, which may be substituted; aralkoxycarbonylamino group such as $NHCOOCH_2C_6H_5$, $NHCOOCH_2CH_2C_6H_5$, $N(CH_3)COOCH_2C_6H_5$, $N(_2H_5)COOCH_2C_6H_5$, $NHCOOCH_2C_6H_4CH_3$, $NHCOOCH_2C_6H_4OCH_3$ and the like, the aralkoxycarbonylamino group may be substituted; aryloxycarbonylamino group such as $NHCOOC_6H_5$, $NHCOOC_6H_5$, $NCHOOC_6H_5$, $NC_2H_5COOC_6H_5$, $NCHCOOC_6H_4CH_3$, $NHCOOC_6H_4OCH_3$ and the like, the aryloxycarbonylamino group may be substituted; alkoxycarbonylamino group such as $NHCOOc_2H_5$, $NHCOOCH_3$ and the like, the alkoxycarbonylamino group may be substituted; carboxylic acid or its derivatives such as amides, like $CONH_2$, CONHMe, $CONMe_2$, CONMEt, $CONEt_2$, CONHPh and the like, the carboxylic acid derivatives may be substituted; acyloxy group such as OOCMe, OOCEt, OOCPh and the like which may optionally be substituted; sulfonic acid or its derivatives such as $SO_2NH_2$, $SO_2NHMe$, $SO_2NMe_2$, $SO_2NHCF_3$ and the like, the sulfonic acid derivatives may be substituted.

When the groups represented by $R^1$–$R^4$ are substituted, the substituents maybe selected from halogen, hydroxy, or nitro or unsubstituted or substituted groups selected from alkyl, cycloalkyl, alkoxy, cycloalkoxy, aryl, aralkyl, aralkoxy, aryloxy, alkoxyalkyl, aryloxyalkyl, aralkoxyalkyl, heterocyclyl, heteroaryl, heteroaralkyl, acyl, acyloxy, hydroxyalkyl, amino, acylamino, arylamino, aminoalkyl, alkoxycarbonyl, alkylamino, alkylthio, thioalkyl groups, carboxylic acid or its derivatives, or sulfonic acid or its derivatives. These groups are as defined above.

Suitable ring A includes phenyl, naphthyl, cyclohexyl, cyclohexenyl, thienyl, furyl, pyrrolyl, oxazolyl, oxadiazolyl, thiazolyl, imidazolyl, isoxazolyl, pyridyl, pyranyl, dihydropyranyl, pyridazyl, pyrimidinyl and the like; which may be unsubstituted or substituted and substituents are selected from the same group as that of $R^1$–$R^4$ and are defined as they are for $R^1$–$R^4$. Preferred substituents are halogen, hydroxy, amino, formyl, optionally halogenated $(C_1$–$C_6)$alkyl, $(C_1$–$C_6)$alkoxy, cyclo$(C_3$–$C_6)$alkyl, cyclo $(C_3$–$C_6)$alkoxy, aryl, aralkyl, aralkoxy, heterocyclyl, acyl, acyloxy, carboxyl, alkoxycarbonyl, aralkoxycarbonyl, alkylamino, acylamino, aralkoxycarbonylamino or aminocarbonyl groups.

It is preferred that cyclic structure represented by ring A is a phenyl or a pyridyl ring.

It is still more preferred that the cyclic s represented by ring A is a phenyl ring.

Suitable X includes oxygen, sulfur or a group $NR^9$, preferably oxygen and sulfur. Suitably, $R^9$ represents hydrogen, $(C_1$–$C_6)$, $(C_3$–$C_6)$ cycloalkyl, aralkyl a group such as benzyl, phenethyl; acyl getup such as acetyl, propanoyl, butanoyl, benzoyl and the like; $(C_1$–$C_6)$ alkoxycarbonyl; aryloxycarbonyl such as phenoxycarbonyl, $CH_3OC_6H_4OCO$, Hal-$C_6H_4OCO$, $CH_3C_6H_4OCO$, naphthyloxycarbonyl and the like; aralkoxycarbonyl such as benzyloxycarbonyl, phenethyloxycarbonyl and the like; the groups represented by $R^9$ may be substituted or unsubstituted. When the groups represented by $R^9$ are substituted, the substituents may be selected from halogen, optionally halogenated lower alkyl, hydroxy, optionally halogenated $(C_1$–$C_3)$alkoxy groups.

The group represented by Ar includes substituted or unsubstituted groups selected from divalent phenylene, naphthylene, pyridyl, quinolinyl, benzofuryl, benzopyranyl, benzoxazolyl, benzothiazolyl, indolyl, indolinyl, azaindolyl, azaindolinyl, indenyl, dihydrobenzofuryl, dyhydrobenzopyranyl, pyrazolyl and the like. The substituents on the group represented by Ar include linear or branched optionally halogenated ($C_1$–$C_6$)alkyl, optionally halogenated ($C_1$–$C_3$)alkoxy, halogen, acyl, amino, acylamino, thio, carboxylic and sulfonic acids and their derivatives. The substituents are defined as they are for $R^1$–$R^4$.

It in more preferred that Ar represents a substituted or unsubstituted divalent phenylene, naphthylene, benzofuranyl, indolyl, indolinyl, quinolinyl, azaindolyl, azaindolinyl, benzothiazolyl or benzoxazolyl groups.

It in still more preferred that Ar to divalent phenylene or benzofuranyl, which may be unsubstituted or substituted by methyl, halomethyl, methoxy or halomethoxy groups.

Suitable $R^5$ includes hydrogen, lower alkyl, groups such as methyl, ethyl or propyl; hydroxy, ($C_1$–$C_3$)alkoxy; halogen atom such as fluorine, chlorine, bromine or iodine; aralkyl such as benzyl, phenethyl, which may be unsubstituted or substituted with halogen, hydroxy, ($C_1$–$C_3$)alkyl, ($C_1$–$C_3$) alkoxy, benzyloxy, acetyl, acetyloxy groups or $R^5$ together with $R^6$ represent a bond.

Suitable $R^6$ may be hydrogen, lower alkyl, groups such as methyl, ethyl or propyl; hydroxy, ($C_1$–$C_3$)alkoxy; halogen atom such as fluorine, chlorine, bromine or iodine; acyl group such as linear or branched ($C_2$–$C_{10}$)acyl group such as acetyl, propanoyl, butanoyl, pentanoyl, benzoyl and the like; aralkyl such as benzyl, phenethyl, which may be unsubstituted or substituted with halogen, hydroxy, ($C_1$–$C_3$)alkyl, ($C_1$–$C_3$)alkoxy, benzyloxy, acetyl, acetyloxy groups or together with $R^5$; forms a bond.

It is preferred that $R^5$; and $R^6$ represent hydrogen atom or $R^5$ and $R^6$ together represent a bond.

Suitable groups represented by $R^7$ may be selected from hydrogen, linear or branched ($C_1$–$C_{16}$)alkyl, preferably ($C_1$–$C_{12}$)alkyl group such as methyl, ethyl, n-propyl, isopropyl, n butyl, iso-butyl, pentyl, hexyl, octyl and the like, the alkyl, group may be substituted; ($C_1$–$C_7$)cycloalkyl group such as cyclopropyl, cyclobutyl, cyclopentyl, cyclohexyl, and the like, the cycloalkyl group may be substituted; aryl group such as, phenyl, naphthyl, the aryl group may be substituted; heteroaryl group such as pyridyl, thienyl, furyl and the like, the heteroaryl group may be substituted; heteroaralkyl group such as furanmethyl, pyridinemethyl, oxazolemethyl, oxazolethyl and the like, the heteroaralkyl group may be substituted; aralkyl group wherein the aryl group is an defined earlier and the alkyl, moiety may contain $C_1$–$C_6$ atoms such as benzyl, phenethyl and the like, wherein the aralkyl group may be substituted; heterocyclyl group such as aziridinyl, pyrrolidinyl, piperidinyl and the like, the heterocyclyl group may be substituted; ($C_1$–$C_6$)alkoxy($C_1$–$C_6$)alkyl group such as methoxymethyl, ethoxymethyl, methoxyethyl, ethoxypropyl and the like, the alkoxyalkyl group may be substituted; acyl group such as acetyl, propanoyl, butanoyl, benzoyl and the like, the acyl group may be substituted; ($C_1$–$C_6$) (alkoxycarbonyl such as methoxycarbonyl, ethoxycarbonyl and the like, the alkoxycarbonyl group may be substituted; aryloxycarbonyl such as phenoxycarbonyl, naphthyloxycarbonyl and the like, the arytoxycarbonyl group may be substituted; ($C_1$–$C_6$) alkylaminocarbonyl, the alkyl group may be substituted; arylaminocarbonyl such as PhNHCO, naphthylaminocarbonyl, the aryl moiety may be substituted. The substituents may be selected from halogen, hydroxy, or vitro or unsubstituted or substituted groups selected from alkyl, cycloalkyl, alkoxy, cycloalkoxy, aryl, aralkyl, aralkoxyalkyl, heterocyclyl, heteroaryl, heteroaralkyl acyl, acyloxy, hydroxyalkyl, amino, acylamino, arylamino, aminoalkyl, aryloxy, aralkoxy, alkoxycarbonyl, alkylamino, alkoxyalkyl, aryloxyalkyl, alkylthio, thioalkyl groups, carboxylic acid or its derivatives, or sulfonic acid or its derivatives. These substituents are as defined above.

Suitable groups represented by $R^8$ may be selected from hydrogen, linear or branched ($C_1$–$C_{16}$)alkyl, preferably ($C_1$–$C_{12}$)alkyl group such as methyl, ethyl, a propyl, isopropyl, n-butyl, iso-butyl, pentyl, hexyl, octyl and the like; ($C_3$–$C_7$)cycloalkyl such as cyclopropyl, cyclopentyl, cyclohexyl and the like, the cycloalkyl group may be substituted; aryl group such as phenyl, naphthyl, the aryl group may be substituted; heteroaryl group such as pyridyl, thienyl, furyl and the like, the heteroaryl group may be substituted; heteroaralkyl group such as furanmethyl, pyridinemethyl, oxazolemethyl, oxazolethyl and the like, the heteroaralkyl group may be substituted; aralkyl group such as benzyl, phenethyl and the like, the aralkyl group may be substituted; heterocyclyl group such as aziridinyl, pyrrolidinyl, piperidinyl and the like, the heterocyclyl group may be substituted, The substituents may be selected from halogen, hydroxy, formyl or vitro or unsubstituted or substituted groups selected from alkyl, cycloalkyl, alkoxy, cycloalkoxy, aryl, aralkyl, aralkoxyalkyl, heterocyclyl, heteroaryl, heteroaralkyl, acyl, acyloxy, hydroxyalkyl, amino, acylamino, arylamino, aminoalkyl, aryloxy, aralkoxy, alkoxycarbonyl, alkylamino, alkoxyalkyl, aryloxyalkyl, alkylthio, thioalkyl groups, carboxylic acid or its derivatives, or sulfonic acid or its derivatives. These substituents are as defined above.

Suitable groups represented by $R^{10}$ may be selected from hydrogen, linear or branched ($C_1$–$C_{16}$)alkyl; preferably ($C_1$–$C_{12}$)alkyl; hydroxy($C_1$–$C_6$)alkyl; aryl group such as phenyl, naphthyl and the like; aralkyl group such as benzyl, phenethyl and the like; heterocyclyl group such as aziridinyl, pyrrolidinyl, piperidinyl, and the like; heteroaryl group such as pyridyl, thienyl, furyl and the like; heteroaralkyl group such as furanmethyl, pyridinemethyl, oxazolemethyl, oxazolethyl and the like.

Suitable ring structures formed by $R^8$ and $R^{10}$ together may be selected from pyrrolidinyl, piperidinyl, morpholinyl, piperazinyl and the like.

Suitable m in an integer ranging from 0–1. It is preferred that when m=0, Ar represents a divalent benzofuranyl, benzoxazolyl, benzothiazolyl, indolyl, indolinyl, dihydrobenzofuryl, dyhydrobenzopyranyl groups, preferably benzofuranyl group and when m=1, Ar represents divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dyhydrobenzopyranyl, pyrazolyl groups.

It is preferred that when m=0, Ar represents a divalent benzofuranyl group, more preferably benzofuran-2,5-diyl group, and when m=1, Ar represents a phenylene group.

Suitable n is an integer ranging from 1 to 4, preferably n represents an integer 1 or 2.

It is preferred that when m=1, n represents 2.

It is also preferred that when m=0, n represents 1.

Pharmaceutically acceptable salts forming part of this invention include salts of the carboxylic acid moiety such as alkali metal salts like Li, Na, and K salts; alkaline earth metal salts (I), Ca and Mg salts; salts of organic bases such as diethanolamine, choline and the like; chiral bases like alkyl phenyl amine, phenyl glycinol and the like; natural aminoacids such as lysine, arginine, guanidine, and the like; unnatural aminoacids such as D-isomers or substituted aminoacids; ammonium or substituted ammonium salts and aluminum salts. Salts may include acid addition salts where appropriate which are, sulphates, nitrates, phosphates, perchlorates, borates, hydrohalides, acetates, tartrates, maleates, citrates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

The pharmaceutically acceptable salts forming part of this invention are found to have good solubility which is one of the essential properties for pharmaceutical compounds.

Particularly useful compounds according to the present invention include

Ethyl (E/Z)-3-[4-[2-(Phenothiazin-10-yl)ethoxy]phenyl]-2-ethoxypropenoate;
Ethyl (E)-3-[4-[2-(Phenothiazin-10-yl)ethoxy]phenyl]-2-ethoxypropenoate;
Ethyl (Z)-3-[4-[2-(Phenothiazin-10-yl)ethoxy]phenyl]-2-ethoxypropenoate;

Ethyl(E/Z)-3-[2-(phenothiazin-10-yl)metlylbenzofuran-5-yl]-2-ethoxypropenoate;
Ethyl(E)-3-[2-(phenothiazin-10-yl)metlylbenzofuran-5-yl]-2-ethoxypropenoate;
Ethyl(Z)-3-[2-(phenothiazin-10-yl)metlylbenzofuran-5-yl]-2-ethoxypropenoate;

Ethyl(E/Z)-3-[4-[2-(phenoxazin-10-yl)ethoxy]phenyl]-2ethoxypropenoate;
Ethyl(E)-3-[4-[2-(phenoxazin-10-yl)ethoxy]phenyl]-2ethoxypropenoate;
Ethyl(Z)-3-[4-[2-(phenoxazin-10-yl)ethoxy]phenyl]-2ethoxypropenoate;

(±)Methyl 3-[4-[2-(phenothiazin-10-yl)ethoxy]phenyl]-2-ethoxypropanoate;
(+)Methyl 3-[4-[2-(phenothiazin-10-yl)ethoxy]phenyl]-2-ethoxypropanoate;
(−)Methyl 3-[4-[2-(phenothiazin-10-yl)ethoxy]phenyl]-2-ethoxypropanoate;

(±)Methyl 3-[2-(phenothiazin-10-yl)methylbenzofuran-5-yl]-2-ethoxypropanoate;
(+)Methyl 3-[2-(phenothiazin-10-yl)methylbenzofuran-5-yl]-2-ethoxypropanoate;
(−)Methyl 3-[2-(phenothiazin-10-yl)methylbenzofuran-5-yl]-2-ethoxypropanoate;

(±)Methyl 3-[4-[2-(phenoxazin-10-yl)ethoxy]phenyl]-2-ethoxypropanoate;
(+)Methyl 3-[4-[2-(phenoxazin-10-yl)ethoxy]phenyl]-2-ethoxypropanoate;
(−)Methyl 3-[4-[2-(phenoxazin-10-yl)ethoxy]phenyl]-2-ethoxypropanoate;

(±)Ethyl 3-[4-(2-(phenoxazin-10-yl)ethoxy]phenyl]-2-ethoxypropanoate;
(+)Ethyl 3-[4-(2-(phenoxazin-10-yl)ethoxy]phenyl]-2-ethoxypropanoate;
(−)Ethyl 3-[4-(2-(phenoxazin-10-yl)ethoxy]phenyl]-2-ethoxypropanoate;

(±)Ethyl 3-[4-[2-(phenoxazin-10-yl)ethoxy]phenyl]-2-hydroxypropanoate;
(+)Ethyl 3-[4-[2-(phenoxazin-10-yl)ethoxy]phenyl]-2-hydroxypropanoate;
(−)Ethyl 3-[4-[2-(phenoxazin-10-yl)ethoxy]phenyl]-2-hydroxypropanoate;

(±)Ethyl 3-[4-[2-(phenoxazin-10-yl)ethoxy]phenyl]-2-butoxypropanoate;
(+)Ethyl 3-[4-[2-(phenoxazin-10-yl)ethoxy]phenyl]-2-butoxypropanoate;
(−)Ethyl 3-[4-[2-(phenoxazin-10-yl)ethoxy]phenyl]-2-butoxypropanoate;

(±)Ethyl 3-[4-[2-(phenoxazin-10-yl)ethoxy]phenyl]-2-hexyloxypropanoate;
(+)Ethyl 3-[4-[2-(phenoxazin-10-yl)ethoxy]phenyl]-2-hexyloxypropanoate;
(−)Ethyl 3-[4-[2-(phenoxazin-10-yl)ethoxy]phenyl]-2-hexyloxypropanoate;

(±)Ethyl 3-[4-[2-(phenoxazin-10-yl)ethoxy]phenyl]-2-phenoxypropanoate;
(+)Ethyl 3-[4-[2-(phenoxazin-10-yl)ethoxy]phenyl]-2-phenoxypropanoate;
(−)Ethyl 3-[4-[2-(phenoxazin-10-yl)ethoxy]phenyl]-2-phenoxypropanoate;

(±)3-[4-[2-(Phenothiazin-10-yl)ethoxy]phenyl]-2-ethoxypropanoic acid and its salts;
(+)3-[4-[2-(Phenothiazin-10-yl)ethoxy]phenyl]-2-ethoxypropanoic acid and its salts;
(−)3-[4-[2-(Phenothiazin-10-yl)ethoxy]phenyl]-2-ethoxypropanoic acid and its salts;

(±)3-[4-[2-(Phenothiazin-10-yl)ethoxy]phenyl]-2-ethoxy-2-methylpropanoic acid and its salts;
(+)3-[4-[2-(Phenothiazin-10-yl)ethoxy]phenyl]-2-ethoxy-2-methylpropanoic acid and its salts;
(−)3-[4-[2-(Phenothiazin-10-yl)ethoxy]phenyl]-2-ethoxy-2-methylpropanoic acid and its salts;

(±)3-[4-[2-(Phenothiazin-10-yl)ethoxy]phenyl]-2-phenoxypropanoic acid and its salts;
(+)3-[4-[2-(Phenothiazin-10-yl)ethoxy]phenyl]-2-phenoxypropanoic acid and its salts;
(−)3-[4-[2-(Phenothiazin-10-yl)ethoxy]phenyl]-2-phenoxypropanoic acid and its salts;

(±)3-[4-[2-(Phenothiazin-10-yl)ethoxy]phenyl]-2-phenoxy-2-methylpropanoic acid and its salts;
(+)3-[4-[2-(Phenothiazin-10-yl)ethoxy]phenyl]-2-phenoxy-2-methylpropanoic acid and its salts;
(−)3-[4-[2-(Phenothiazin-10-yl)ethoxy]phenyl]-2-phenoxy-2-methylpropanoic acid and its salts;

(±)3-[2-(Phenothiazin-10-yl)methylbenzofuran-5-yl]-2-ethoxypropanoic acid and its salts;
(+)3-[2-(Phenothiazin-10-yl)methylbenzofuran-5-yl]-2-ethoxypropanoic acid and its salts;
(−)3-[2-(Phenothiazin-10-yl)methylbenzofuran-5-yl]-

(±)3-[4-[2-(Phenoxazin-10-yl)ethoxy]phenyl]-2-ethoxypropanoic acid and its salts;
(+)3-[4-[2-(Phenoxazin-10-yl)ethoxy]phenyl]-2-ethoxypropanoic acid and its salts;
(−)3-[4-[2-(Phenoxazin-10-yl)ethoxy]phenyl]-2-ethoxypropanoic acid and its salts;

(±)3-[4-[2-(Phenoxazin-10-yl)ethoxy]phenyl]-2-ethoxy-2-methylpropanoic acid and its salts;
(+)3-[4-[2-(Phenoxazin-10-yl)ethoxy]phenyl]-2-ethoxy-2-methylpropanoic acid and its salts;
(−)3-[4-[2-(Phenoxazin-10-yl)ethoxy]phenyl]-2-ethoxy-2-methylpropanoic acid and its salts;

(±)3-[4-[2-(Phenoxazin-10-yl)ethoxy]phenyl]-2-phenoxypropanoic acid and its salts;
(+)3-[4-[2-(Phenoxazin-10-yl)ethoxy]phenyl]-2-phenoxypropanoic acid and its salts;
(−)3-[4-[2-(Phenoxazin-10-yl)ethoxy]phenyl]-2-phenoxypropanoic acid and its salts;

(±)3-[4-[2-(Phenoxazin-10-yl)ethoxy]phenyl]-2-phenoxy-2-methylpropanoic acid and its salts;
(+)3-[4-[2-(Phenoxazin-10-yl)ethoxy]phenyl]-2-phenoxy-2-methylpropanoic acid and its salts;
(−)3-[4-[2-(Phenoxazin-10-yl)ethoxy]phenyl]-2-phenoxy-2-methylpropanoic acid and its salts;

(±)3-[4-[2-(Phenoxazin-10-yl)ethoxy]phenyl]-2-hydroxypropanoic acid and its salts;
(+)3-[4-[2-(Phenoxazin-10-yl)ethoxy]phenyl]-2-hydroxypropanoic acid and its salts;
(−)3-[4-[2-(Phenoxazin-10-yl)ethoxy]phenyl]-2-hydroxypropanoic acid and its salts;

(±)3-[4-[2-(Phenoxazin-10-yl)ethoxy]phenyl]-2-butoxypropanoic acid and its salts;
(+)3-[4-[2-(Phenoxazin-10-yl)ethoxy]phenyl]-2-butoxypropanoic acid and its salts;
(−)3-[4-[2-(Phenoxazin-10-yl)ethoxy]phenyl]-2-butoxypropanoic acid and its salts;

(±) 3-[4-[2-(Phenoxazin-10-yl)ethoxy]phenyl]-2-hexyloxypropanoic acid and its salts;

(+) 3-[4-[2-(Phenoxazin-10-yl)ethoxy]phenyl]-2-hexyloxypropanoic acid and its salts;
(−) 3-[4-[2-(Phenoxazin-10-yl)ethoxy]phenyl]-2-hexyloxypropanoic acid and its salts;

(±) 3-[4-[2-(Phenoxazin-10-yl)ethoxy]phenyl]-2-phenoxypropanoic acid and its salts;
(+) 3-[4-[2-(Phenoxazin-10-yl)ethoxy]phenyl]-2-phenoxypropanoic acid and its salts;
(−) 3-[4-[2-(Phenoxazin-10-yl)ethoxy]phenyl]-2-phenoxypropanoic acid and its salts;
[(2R)-N(1S)]-3-[4-[2-(Phenoxazin-10-yl)ethoxy]phenyl]-2-ethoxy-N-(2-hydroxy-1-phenyl ethyl)propanamide;
[(2S)-N(1S)]-3-[4-[2-(Phenoxazin-10-yl)ethoxy]phenyl]-2-ethoxy-N-(2-hydroxy-1-phenyl ethyl)propanamide;
[(2S)-N(1S)]-3-[4-[2-(phenothiazin-10-yl)ethoxy]phenyl]-2-ethoxy-N-(2-hydroxy-1-phenyl ethyl)propanamide and
[(2R)-N(1S)]-3-[4-[2-(phenothiazin-10-yl)ethoxy]phenyl]-2-ethoxy-N-(2-hydroxy-1-phenyl ethyl)propanamide.

According to a feature of the present invention, the compound of general formula (III) where $R^1$, $R^2$, $R^3$, $R^4$, $R^5$, $R^6$, $R^7$, $R^8$, X, A, n, m, Ar are as defined earlier can be prepared by any of the following routes shown in Scheme I. The compound of general formula (III) represent a compound of general formula (I), wherein all the symbols are as defined earlier and $R^5$ and $R^6$ together represent a bond and Y represents oxygen atom.

Scheme-I

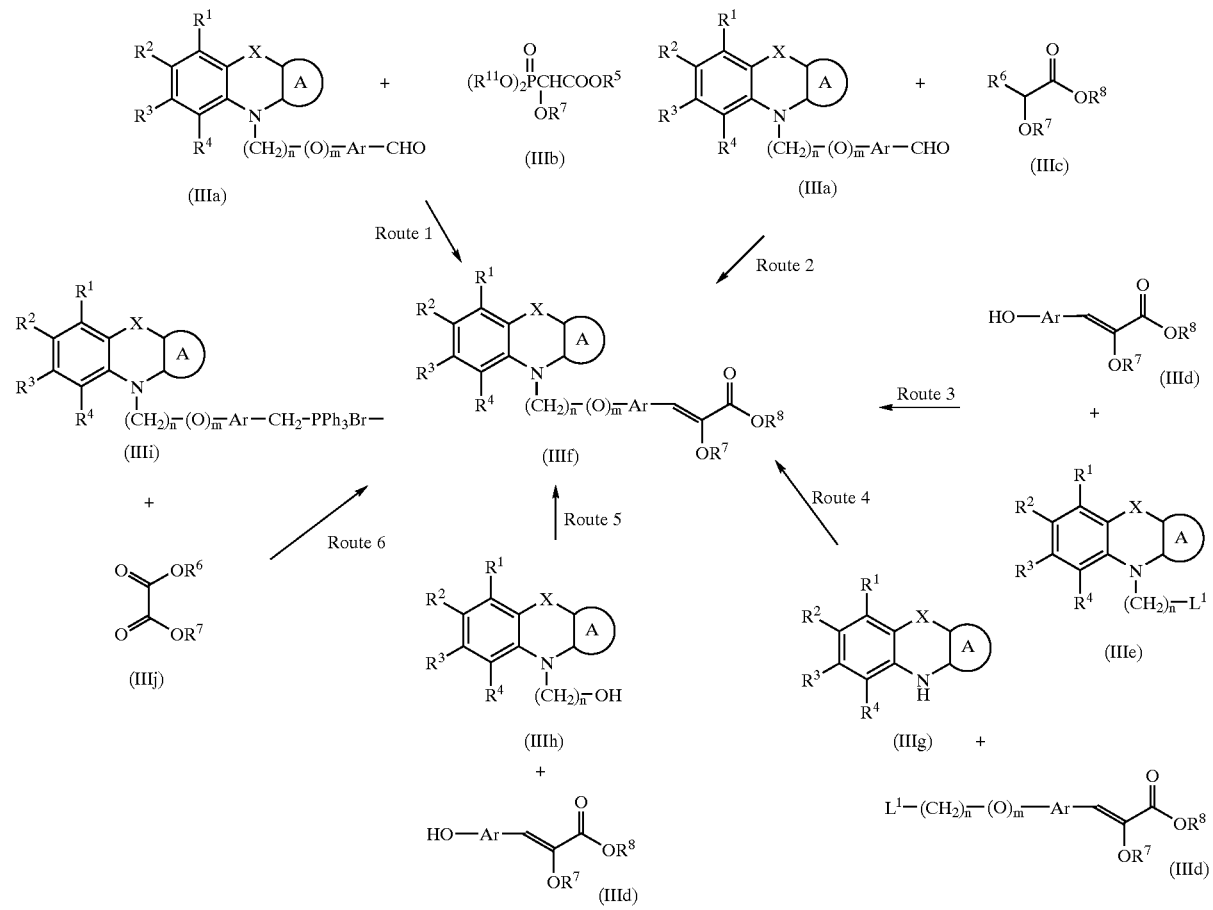

Route (1): The reaction of a compound of the general formula (IIIa) where all symbols are as defined earlier with a compound of formula (IIIb), where $R^{11}$ may be a lower alkyl group and $R^7$ and $R^8$ are as defined earlier excluding hydrogen, to yield a compound of general formula (III) may be carried out in the presence of a base such as alkali metal hydrides like NaH, KH or organolithiums like $CH_3Li$, BuLi and the like or alkoxides such as NaOMe, NaOEt, $K^+BuO^-$ or mixtures thereof. The reaction may be carried out in presence of solvents such as THF, dioxane, DMF, DMSO, DME and the like or mixture thereof. HMPA may be used as cosolvent. The reaction temperature may range from −78° C. to 50° C., preferably at a temperature in the range of −10° C. to 30° C. The compound of general formula (III b) may be prepared according to the procedure described in the literature (Annalen. Chemie, (1996) 53, 699).

Alternatively, the compound of formula (III) may be prepared by reacting the compound of formula (IIIa) where all symbols are as defined earlier with Wittig reagents such as $Hal^- PH_3P^+CH—(OR^7)CO_2R^8$ under similar reaction conditions as described above.

Route (2): The reaction of a compound of the general formula (IIIa) where all symbols are as defined earlier with a compound of formula (IIIc) where $R^6$ represents a hydrogen atom and $R^7$ and $R^8$ are as defined earlier may be carried out in the presence of a base. The base is not critical. Any base normally employed for aldol condensation reaction may be employed; bases like metal hydride such as NaH, KH, metal alkoxides such as NaOMe, $K^+BuO^-$, NaOEt, metal amides such as $LiNH_2$, $LiN(ipr)_2$ may be used. Aprotic solvent such as THF, ether, dioxane may be used. The reaction may be carried out in an inert atmosphere which may be maintained by using inert gases such as $N_2$, Ar, or He and the reaction is more effective under anhydrous conditions. Temperature in the range of −80° C. to 35° C. may be used. The β-hydroxy product initially produced may be dehydrated under conventional dehydration conditions such as treating with PTSA in solvents such as benzene or toluene. The nature of solvent and dehydrating agent is not critical. Temperature in the range of 20° C. to reflux temperature of the solvent used may be employed, preferably at reflux temperature of the solvent by continuous removal of water using a Dean Stark water separator.

Route (3): The reaction of compound of formula (IIIe) where $L^1$ is a leaving group such as halogen atom, p-toluenesulfonate, methanesulfonate, trifluoromethanesulfonate and the like and all symbols are as defined earlier with a compound of formula (IIId) where $R^7$, $R^8$ and Ar are as defined earlier to produce a compound of the formula (III) may be carried out in the presence of solvents such as THF, DMF, DMSO, DME and the like or mixtures thereof. The reaction may be carried out in an inert atmosphere which may be maintained by using inert gases such as $Ni_2$, Ar, or He. The reaction may be effected in the presence of a base such as $K_2CO_3$, $Na_2CO_3$ or NaH or mixtures thereof. Acetone may be used as solvent when $Na_2CO_3$ or $K_2CO_3$ is used as a base. The reaction temperature may range from 0° C.–120° C., preferably at a temperature in the range of 30° C.–100° C. The duration of the reaction may range from 1 to 24 hours, preferably from 2 to 12 hours. The compound of formula (IIId) can be prepared according to known procedure by a Wittig Horner reaction between the protected hydroxy aryl aldehyde such as benzyloxyaryl aldehyde and compound of formula (IIIb), followed by reduction of double blood and deprotection.

Route (4): The reaction of a compound of general formula (IIIg) where all symbols are as defined earlier with a compound of general formula (IIIf) where all symbols are as defined earlier and $L^1$ is a leaving group such as halogen atom, p-toluenesulfonate, methanesulfonate, trifluoromethanesulfonate and the like, preferably a halogen atom to produce a compound of general formula (III) may be carried out in the presence of solvents such as DMSO, DMF, DME, THF, dioxane, ether and the like or a combination thereof. The reaction may be carried out in an inert atmosphere which may be maintained by using inert gases such as $N_2$, Ar, He. The reaction may be effected in the presence of a base such as alkalis like sodium hydroxide, potassium hydroxide and the like, alkali metal carbonate like sodium carbonate, potassium carbonate and the like; alkali metal hydrides such as sodium hydride, potassium hydride and the like; organometallic bases like n-butyl lithium, alkali metal amides like sodamide or mixtures thereof. The amount of base may range from 1 to 5 equivalents, based on the amount of the compound of formula (IIIg), preferably the amount of base ranges from 1 to 3 equivalents. Phase transfer catalysts such as tetraalkylammonium halide or hydroxide may be added. The reaction may be carried out at a temperature in the range of 0° C. to 150° C., preferably at a temperature in the range of 15° C. to 100° C. The duration of the reaction may range from 0.25 to 48 hours, preferably from 0.25 to 12 hours.

Route (5): The reaction of compound of general formula (IIIh) where all symbols are as defined earlier with a compound of general formula (IIId) where all symbols are as defined above may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetronitrile, carbontetrachloride and the like. The inert atmosphere may be maintained by using inert gases such as $N_2$, Ar, He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

Route 6: The reaction of a compound of formula (IIIi) where all symbols are as defined earlier with a compound of formula (IIIj) where $R^7=R^8$ and are as defined earlier excluding hydrogen, to produce a compound of the formula (III) where all symbols are as defined earlier may be carried out neat in the presence of a base such as alkali metal hydrides like NaH or KH or organolithiums like $CH_3Li$, BuLi and the like or alkoxides such as NaOMe, NaOEt, $K^+BuO^-$ and the like or mixtures thereof. The reaction may be carried out in the presence of aprotic solvents such as THF, dioxane, DMF, DMSO, DME and the like or mixture thereof. HMPA may be used as cosolvent. The reaction temperature may range from −78° C. to 100° C., preferably at a temperature in the range of −10° C. to 50° C.

According to another embodiment of the present invention, the compound of the general formula (I) where $R^5$ represents hydroxy, alkoxy, halogen, lower alkyl or unsubstituted or substituted aralkyl group, $R^6$ represents hydroxy, alkoxy, halogen, lower alkyl group, acyl or unsubstituted or substituted aralkyl group, $R^1$, $R^2$, $R^3$, $R^4$, $R^7$, $R^8$, X, A, n, m, Ar as defined earlier and Y represents oxygen atom can be prepared by one or more of the processes shown in Scheme-II:

Scheme-II

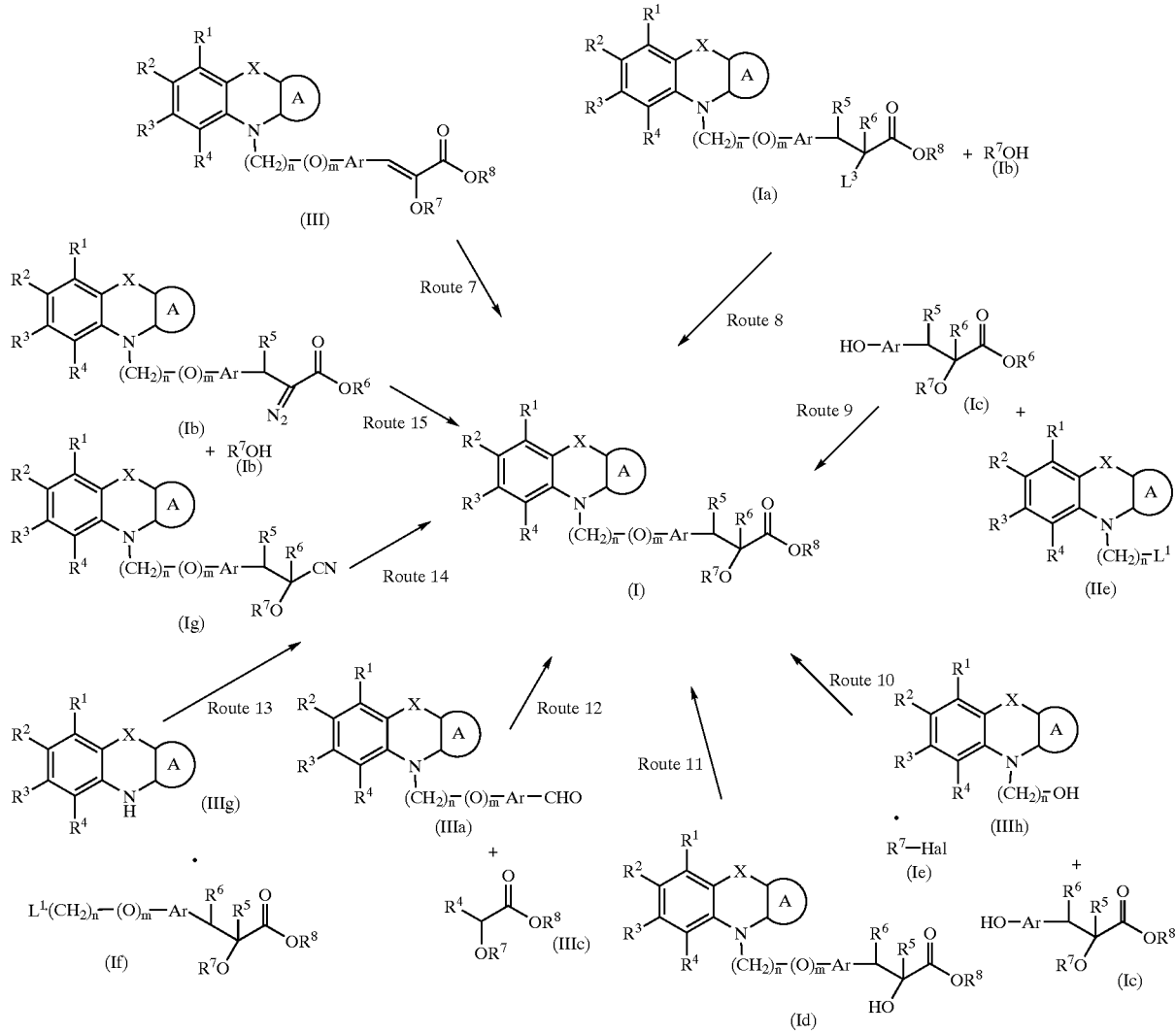

Route (7): The reduction of compound of formula (III) which represents a compound of formula (I) where $R^5$ and $R^6$ together represent a bond and Y represents an oxygen atom and all other symbols are as defined above may be obtained as described earlier in Scheme-I, to yield a compound of the general formula (I) where $R^5$ and $R^6$ each represent hydrogen atom and all symbols are as defined earlier, may be carried out in the presence of gaseous hydrogen and a catalyst such as Pd/C, Rh/C, Pt/C, and the like. Mixtures of catalysts may be used. The reaction may also be conducted in the presence of solvents such as dioxane, acetic acid, ethyl acetate, ethanol and the like. The nature of the solvent is not critical. A pressure between atmospheric pressure and 80 psi may be employed. Higher pressures may be used to reduce the reaction time. The catalyst may be preferably 5–10% Pd/C and the amount of catalyst used may range from 1–100% w/w. The reaction may also be carried out by employing metal solvent reduction such as magnesium in alcohol or sodium amalgam in alcohol. The hydrogenation may be carried out in the presence of metal catalysts containing chiral ligands to obtain a compound of formula (I) in optically active form. The metal catalyst may contain Rhodium, Ruthenium, Indium and the like. The chiral ligands may preferably be chiral phosphines such as (2S,3S)-bis(diphenylphosphino) butane, 1,2-bis(diphenylphosphino)ethane, 1,2-bis(2-methoxyphenylphosphino)ethane, (−)-2,3-isopropylidene-2,3-dihydroxy-1,4-bis(diphenyl phosphino)butane and the like. Any suitable chiral catalyst may be employed which would give required optical purity of the product (I) (Ref: Principles of Asymmetric Synthesis, Tet. Org. Chem. Series Vol 14, pp311–316, Ed. Baldwin J. E.).

Route (8): The reaction of compound of formula (Ia) where $R^8$ is as defined earlier excluding hydrogen and all other symbols are as defined earlier and $L^3$ is a leaving group such as halogen atom with an alcohol of general formula (Ib), where $R^7$ is as defined earlier excluding hydrogen to produce a compound of the formula (I) may be carried out in the presence of solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as KOH, NaOH, NaOMe, NaOEt, $K^+BuO^-$ or NaH or mixtures thereof. Phase transfer catalysts such as tetraalkylammonium halides or hydroxides may be employed. The reaction temperature may range from 20° C.–120° C., preferably at a temperature in the range of 30° C.–100° C. The duration of the reaction may range from 1 to 12 hours, preferably from 2 to 6 hours. The compound of formula (Ia) may be prepared according to the process disclosed in our copending application Ser. No. 08/982,910.

Route (9): The reaction of compound of formula (IIIe) defined earlier with compound of formula (Ic) where all symbols are as defined earlier to produce a compound of the formula (I) may be carried out in the presence of solvents such as THF, DMF, DMSO, DME and the like or mixtures thereoef. The reaction may be carried out in an inert atmosphere which is maintained by using inert gases such as $N_2$, Ar or He. The reaction may be effected in the presence of a base such as $K_2CO_3$, $Na_2CO_3$ or NaH or mixtures thereof. Acetone may be used as a solvent when $K_2CO_3$ or $Na_2CO_3$ is used as a base. The reaction temperature may range from 20° C.–120° C., preferably at a temperature in the range of 30° C.–80° C. The duration of the reaction may range from 1 to 24 hours, preferably from 2 to 12 hours. The compound of formula (Ic) may be prepared by Wittig Horner reaction between the protected hydroxyaryl aldehyde and compound of formula (IIIb) followed by reduction of the double bond and deprotection. Alternatively, the compound of formula (Ic) may be prepared by following a procedure disclosed in WO 94/01420.

Routine (10): The reaction of compound of general formula (IIIh) defined earlier with a compound of general formula (Ic) where all symbols are as defined earlier may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

Route (11): The reaction of compound of formula (Id), which represents a compound of formula (I) where all symbols are as defined earlier, with a compound of formula (Ie) where $R^7$ represents unsubstituted or substituted groups selected from alkyl, cycloalkyl, aryl, aralkyl, alkoxylated, alkoxycarbonyl, aryloxycarbonyl, alkylaminocarbonyl, arylaminocarbonyl, acyl, heterocyclyl, heteroaryl or heteroaralkyl groups and Hal represents Cl, Br, or I, to produce a compound of formula (I) may be carried out in the presence of solvents such as THF, DMF, DMSO, DME and the like. The inert atmosphere may be maintained by using inert gases such as $N_2$, Ar or He. The reaction may be effected in the presence of a base such as KOH, NaOH, NaOMe, $K^+BuO^-$, NaH and the like. Phase transfer catalyst such as tetraalkylammonium halides or hydroxides may be employed. The reaction temperature may range from 20° C. to 150° C., preferably at a temperature in the range of 30° C. to 100° C. The duration of the reaction may range from 1 to 24 hours, preferably from 2 to 12 hours. The compound of formula (Id) represents compound of formula (I) where $R^7$ represents H and Y represents oxygen atom.

Route (12): The reaction of a compound of the general formula (IIIa) defined earlier with a compound of formula (IIIc) where $R^6$, $R^7$ and $R^8$ are as defined earlier may be carried out under conventional conditions. The base is not critical. Any base normally employed for aldol condensation reaction may be employed, like, metal hydrides such as NaH, KH and the like, metal alkoxides such as NaOMe, $K^+BuO^-$, NaOEt and the like, metal amides such as $LiNH_2$, $LiN(ipr)_2$ and the like. Aprotic solvents such as THF, ethers, dioxane may be used. The reaction may be carried out in an inert atmosphere which may be maintained by using inert gases such as $N_2$, Ar, or He and the reaction is more effective under anhydrous conditions. Temperature in the range of −80° C. to 25° C. may be used. The β-hydroxy aldol product may be dehydroxylated using conventional methods, conveniently by ionic hydrogenation technique such as by treating with a trialkyl silane in the presence of an acid such as trifluoroacetic acid. Solvent such as $CH_2Cl_2$ may be used. Favorably, reaction proceeds at 25° C. Higher temperature may be employed if the reaction is slow.

Route (13): The reaction of a compound of general formula (IIIg) where all symbols are as defined earlier with a compound of general formula (If) where $L^1$ is a leaving group such as halogen atom, p-toluenesulfonate, methanesulfonate, trifluoromethanesulfonate and the like, preferably a halogen atom and all other symbols are as defined earlier to produce a compound of general formula (I) may be carried out in the presence of solvents such as DMSO, DMF, DME, THF, dioxane, ether and the like or a combination thereof. The reaction may be carried out in an inert atmosphere which may be maintained by using inert gases such as $N_2$, Ar or He. The reaction may be effected in the presence of a base such as alkalis like sodium hydroxide, potassium hydroxide and the like, alkali metal carbonates like sodium carbonate, potassium carbonate and the like; alkali metal hydrides such as sodium hydride, potassium hydride and the like; organometallic bases like n-butyl lithium, alkali metal amides like sodamide or mixtures thereof. The amount of base may range from 1 to 5 equivalents, based on the amount of the compound of formula (IIIg), preferably the amount of base ranges from 1 to 3 equivalents. The reaction may be carried out in the presence of phase transfer catalysts such as tetraalkylammonium halides or hydroxides. The reaction may be carried out at a temperature in the range of 0° C. to 150° C., preferably at a temperature in the range of 15° C. to 100° C. The duration of the reaction may range from 0.25 to 24 hours, preferably from 0.25 to 12 hours.

Route 14: The conversion of compound of formula (Ig) where all symbols are as defined earlier to a compound of formula (I) where all symbols are as defined earlier may be carried out either in the presence of base or acid and the selection of base or acid is not critical. Any base normally used for hydrolysis of nitrile to acid may be employed, metal hydroxides such as NaOH or KOH in an aqueous solvent or any acid normally used for hydrolysis of nitrile to ester may be employed such as dry HCl in an excess of alcohol such as methanol, ethanol, propanol and the like. The reaction may be carried out at a temperature in the range of 0° C. to reflux temperature of the solvent used, preferably at a temperature in the range of 25° C. to reflux temperature of the solvent used. The duration of the reaction may range from 0.25 to 48 hrs.

Route 15: The reaction of a compound of formula (Ih) where $R^8$ is as defined earlier excluding hydrogen all symbols are as defined earlier with a compound of formula (Ib) where $R^7$ is as defined earlier excluding hydrogen to produce a compound of formula (I) (by a rhodium carbenoid mediated insertion reaction) may be carried out in the presence of rhodium (II) salts such as rhodium (II) acetate. The reaction may be carried out in the presence of solvents such as benzene, toluene, dioxane, ether, THF and the like or a combination thereof or when practicable in the presence of $R^7OH$ as solvent at any temperature providing a convenient rate of formation of the required product, generally at an elevated temperature, such as reflux temperature of the solvent. The inert atmosphere may be maintained by using inert gases such as $N_2$, Ar or He. The duration of the reaction may range from 0.5 to 24 h, preferably from 0.5 to 6 h.

The compound of formula (I) where $R^8$ represents hydrogen atom may be prepared by hydrolysis using conventional methods, a compound of formula (I) where $R^8$ represents all groups defined earlier except hydrogen. The hydrolysis may be carried out in the presence of a base such as $Na_2CO_3$ and a suitable solvent such as methanol, ethanol and the like or mixtures thereof. The reaction may be carried out at a temperature in the range of 20° C.–40° C., preferably at 25° C.–30° C. the reaction time may range from 2 to 12 h, preferably from 4 to 8 h.

The compound of general formula (I) where Y represents oxygen and $R^8$ represents hydrogen or lower alkyl groups and all other symbols are as defined earlier may be converted to compound of formula (I), where Y represents $NR^{10}$ by reaction with appropriate amines of the formula $NHR^8R^{10}$ where $R^8$ and $R^{10}$ are as defined earlier. Alternatively, the compound of formula (I) where $YR^8$ represents OH may be converted to acid halide, preferably $YR^8$=Cl, by reacting with appropriate reagents such as oxalyl chloride, thionyl chloride and the like, followed by treatment with amines of the formula $NHR^8R^{10}$ where $R^8$ and $R^{10}$ are as defined earlier. Alternatively, mixed anhydrides may be prepared from compound of formula (I) where $YR^8$ represents OH and all other symbols are as defined earlier by treating with acid halides such acetyl chloride, acetyl bromide, pivaloyl chloride, dichlorobenzyl chloride and the like. The reaction may be carried out in the presence of suitable base such as pyridine, triethylamine, diisopropyl ethyl amine and the like. Solvents such as halogenated hydrocarbons like $CHCl_3$, $CH_2Cl_2$, hydrocarbons such as benzene, toluene, xylene and the like may be used. The reaction may be carried out at a temperature in the range of –40° C. to 40° C., preferably 0° C. to 20° C. The acid halide or mixed anhydride thus prepared may further be treated with appropriate amines of the formula $NHR^8R^{10}$ where $R^8$ and $R^{10}$ are as defined earlier.

The processes for the preparation of compounds of general formula (IIIa) have been described in a copending application Ser. No. 08/982,910.

As used herein the term neat means the reaction is carried out without the use of solvent.

In another embodiment of the present invention the novel intermediate of formula (If)

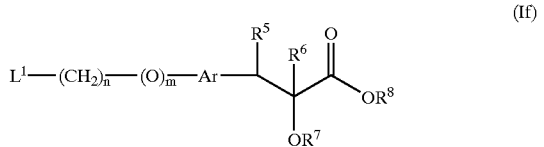

where Ar represents an unsubstituted or substituted divalent single or fused aromatic or heterocyclic group; $R^5$ represents hydrogen atom, hydroxy, alkoxy, halogen, lower alkyl or unsubstituted or substituted aralkyl group or forms a bond together with the adjacent group $R^6$; $R^6$ represents hydrogen, hydroxy, alkoxy, halogen, lower alkyl group, acyl or unsubstituted or substituted aralkyl or $R^6$ forms a bond together with $R^5$; $R^7$ represents hydrogen or unsubstituted or substituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl or heteroaralkyl groups; $R^8$ represents hydrogen or unsubstituted or substituted groups selected from alkyl, cycloalkyl, aryl, aralkyl, heterocyclyl, heteroaryl or heteroaralkyl groups; n is an integer ranging from 1–4; m is an integer 0 or 1 and $L^1$ is a leaving group such as halogen atom, p-toluenesulfonate, methanesulfonate, trifluoromethanesulfonate and the like, preferably a halogen atom and a process for its preparation and its use in the preparation of β-aryl-α-substituted hydroxyalkanoic acids is provided.

The compound of formula (If) where m=0 and all other symbols are as defined may be prepared by reacting a compound of formula (Ic)

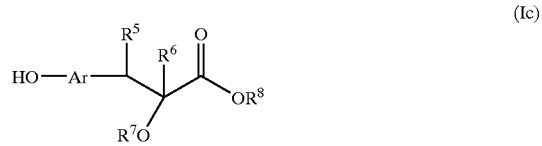

where $R^5$, $R^6$, $R^7$, $R^8$, Ar are as defined earlier, with a compound of formula (Ii)

$$L^1—(CH_2)_n—L^2 \tag{Ii}$$

where $L^1$ and $L^2$ may be same or different and represent a leaving group such as Cl, Br, I, methanesulfonate, trifluoromethanesulfonate, p-toluenesulfonate and the like or $L^2$ may also represent a hydroxy or a protected hydroxy group which may be later converted to a leaving group; n represents an integer ranging from 1–4.

The reaction of compound of formula (Ic) with a compound of formula (Ii) to produce a compound of formula (If) may be carried out in the presence of solvents such as THF, DMF, DMSO, DME and the like or mixtures thereof. The reaction may be carried out in an inert atmosphere, which may be maintained by using inert gases such as $N_2$, Ar or He. The reaction may be effected in the presence of a base such as $K_2CO_3$, $Na_2CO_3$ or NaH or mixtures thereof. Acetone may be used as solvent when $Na_2CO_3$ or $K_2CO_3$ is used as a base. The reaction temperature may range from 20° C.–120° C., preferably at a temperature in the range of 30° C.–80° C. The duration of the reaction may range from 1 to 24 hours, preferably from 2 to 12 hours.

Alternatively, intermediate of formula (If) may be prepared by reacting a compound of formula (Ij)

$$L^1—(CH_2)_n—(O)_m Ar—CHO \tag{Ij}$$

where where $L^1$ represent a leaving group such as Cl, Br, I, methanesulfonate, trifluoromethanesulfonate, p-toluenesulfonate and the like and all other symbols are as defined earlier, with a compound of formula (IIIb)

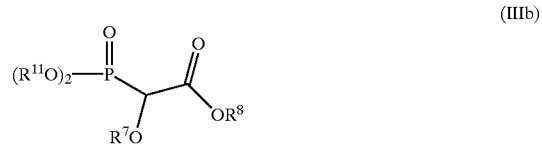

where all symbols are as defined earlier, to yield a compound of formula (IIIf) which is further reduced to yield a compound of formula (If). The compound of formula (IIIf) represents a compound of formula (If) wherein $R^5$ and $R^6$ together represent a bond and all other symbols are as defined earlier.

The reaction of compound of formula (Ij) with (IIIb) may be carried out in the presence of a base such as alkali metal hydrides like NaH, KH or organolithiums like CH₃Li, BuLi and the like or alkoxides such as NaOMe, NaOEt, K⁺BuO⁻ or mixtures thereof. The reaction may be carried out in presence of solvents, such as THF, dioxane, DMF, DMSO, DME and the like or mixtures thereof. HMPA may be used as cosolvent The reaction temperature may range from −78° C. to 50° C., preferably at a temperature in the range of −10° C. to 30° C. The reduction of compound of the formula (IIIf) may be carried out in the presence of gaseous hydrogen and a catalyst such as PD/C, Rh/C, Pt/C, and the like. Mixtures of catalysts may be used. The reaction may also be conducted in the presence of solvents such as dioxane, acetic acid, ethyl acetate, ethanol and the like. The nature of the solvent is not critical. A pressure between atmospheric pressure and 80 psi may be employed. Higher pressures may be used to reduce the reaction time. The catalyst may be preferably 5–10% Pd/C and the amount of catalyst used may range from 1–100% w/w. The reaction may also be carried out by employing metal solvent reduction such as magnesium in alcohol or sodium amalgam in alcohol.

In another embodiment of the present invention there is provided a novel intermediate of formula (Ig)

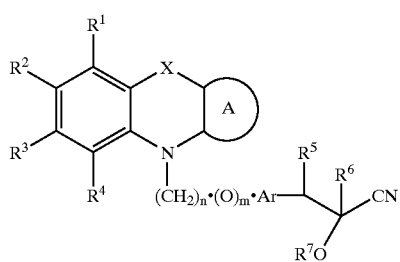

(Ig)

where $R^1$, $R^2$, $R^3$, $R^4$ may be same or different and represent hydrogen, halogen, hydroxy, nitro, cyano, formyl or unsubstituted or substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycrbonylamino, carboxylic acid or its derivatives, or sulfonic acid or its derivatives; the ring A fused to the ring containing X and N represents a 5–6 membered cyclic structure containing carbon atoms, which may optionally contain one or more heteroatoms selected from oxygen, sulfur or nitrogen atoms, which may optionally be substituted; the ring A may be saturated or contain one or more double bonds or may be aromatic; X represents a heteroatom selected from oxygen, sulfur or $NR^9$ where $R^9$ is hydrogen, alkyl, aryl, aralkyl, acyl, alkoxycarbonyl, aryloxycarbonyl or aralkoxycarbonyl groups; Ar represents an unsubstituted or substituted divalent single or fused aromatic or heterocyclic group; $R^5$ represents hydrogen atom, hydroxy, alkoxy, halogen, lower alkyl or unsubstituted or substituted aralkyl group or forms a bond together with the adjacent group $R^6$; $R^6$ represents hydrogen, hydroxy, alkoxy, halogen, lower alkyl group, acyl or unsubstituted or substituted aralkyl or $R^6$ forms a bond together with $R^5$; $R^7$ represents hydrogen or unsubstituted or substituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl or heteroaralkyl groups; n is an integer ranging from 1–4 and m is an integer 0 or 1, a process for its preparation and its use in the preparation of β-aryl-α-substituted hydroxyalkanoic acids.

The compound of formula (Ig) where $R^5$ and $R^6$ each represent hydrogen atoms and all other symbols are as defined earlier is prepared by a process outlined in Scheme-III.

Scheme III

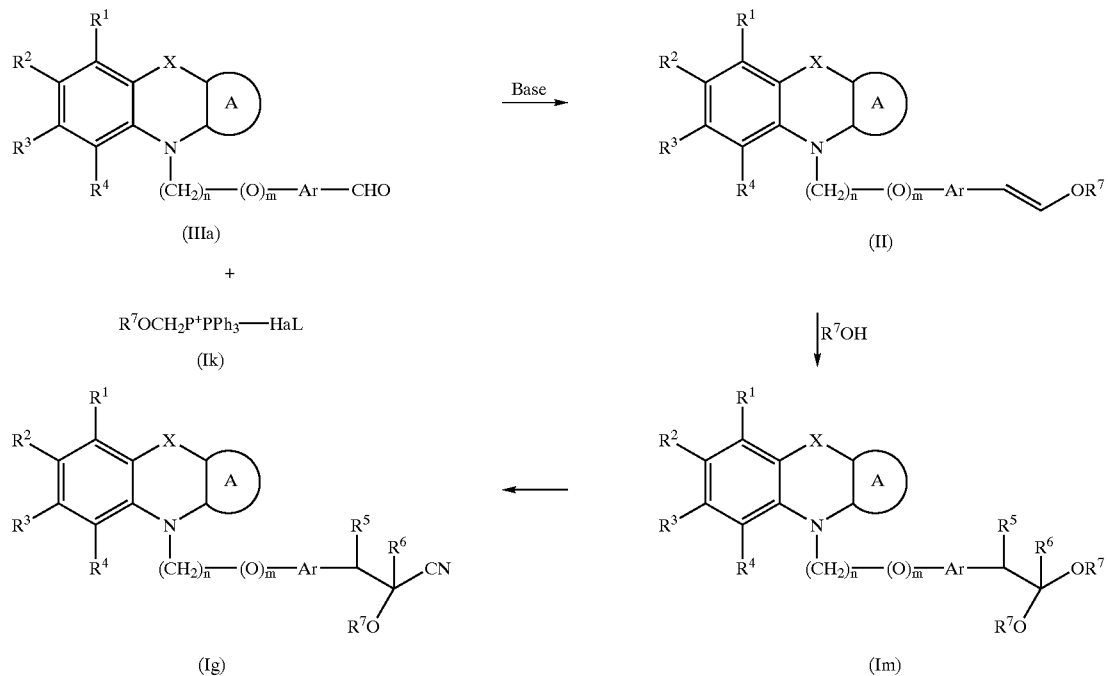

The reaction of a compound of formula (IIIa) where all symbols are as defined earlier with a compound of formula (Ik) where $R^7$ is as defined earlier excluding hydrogen and Hal represent a halogen atom such as Cl, Br or I to produce a compound of formula (Il) may be carried out under conventional conditions in the presence of a base. The base is not critical. Any base normally employed for Wittig reaction may be employed, metal hydride such as NaH or KH; metal alkoxides such as NaOMe, $K^+BuO^-$ or NaOEt; metal amides such as $LiNH_2$ or $LiN(iPr)_2$. Aprotic solvent such as THF, DMSO, dioxane, DME and the like may be used. Mixture of solvents may be used. HMPA may be used as cosolvent. Inert atmosphere may be employed such as argon and the reaction is more effective under anhydrous conditions. Temperature in the range of $-80°$ C. to $100°$ C. may be used.

The compound of (Il) where all symbols are as defined earlier and $R^7$ is as defined earlier excluding hydrogen may be converted to a compound of formula (Im) where $R^5$ and $R^6$ represent hydrogen atoms and all other symbols are as defined earlier, by treating with an alcohol of formula $R^7OH$ where $R^7$ represents unsubstituted or substituted groups selected from alkyl, cycloalkyl, aryl, aralkyl, alkoxyalkyl, alkoxycarbonyl, aryloxycarbonyl, alkylaminocarbonyl, arylaminocarbonyl, acyl, heterocyclyl, heteroaryl or heteroaralkyl under anhydrous conditions in the presence of a strong anhydrous acid such as p-toluenesulfonic acid.

The compound of formula (Im) defined above upon treatment with trialkylsilyl cyanide such as trimethylsilyl cyanide produces a compound of formula (Ig) where $R^5$ and $R^6$ represent hydrogen atoms, $R^7$ is as defined earlier excluding hydrogen and all other symbols are as defined earlier.

In still another embodiment of the present invention the novel intermediate of formula (Ih)

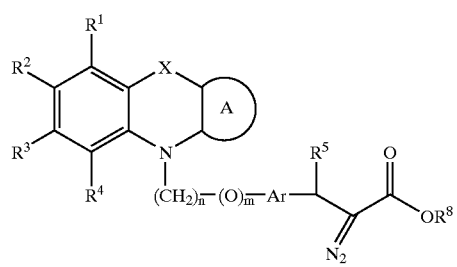

(Ih)

where $R^1$, $R^2$, $R^3$, $R^4$ may be same or different and represent hydrogen, halogen, hydroxy, nitro, cyano, formyl or unsubstituted or substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; the ring A fused to the ring containing X and N represents a 5–6 membered cyclic structure containing carbon atoms, which may optionally contain one or more heteroatoms selected from oxygen, sulfur or nitrogen atoms, which may optionally be substituted; the ring A may be saturated or contain one or more double bonds or may be aromatic; X represents a heteroatom selected from oxygen, sulfur or $NR^9$ where $R^9$ is hydrogen, alkyl, aryl, aralkyl, acyl, alkoxycarbonyl, aryloxycarbonyl or aralkoxycarbonyl groups; Ar represents an unsubstituted or substituted divalent single or fused aromatic or heterocyclic group; $R^5$ represents hydrogen atom, hydroxy, alkoxy, halogen, lower alkyl or unsubstituted or substituted aralkyl group or forms a bond together with the adjacent group $R^6$; $R^6$ represents hydrogen, hydroxy, alkoxy, halogen, lower alkyl group, acyl or unsubstituted or substituted aralkyl or $R^6$ forms a bond together with $R^5$; $R^8$ represents hydrogen or unsubstituted or substituted groups selected from alkyl, cycloalkyl, aryl, aralkyl, heterocyclyl, heteroaryl or heteroaralkyl groups; n is an integer ranging from 1–4 and m is an integer 0 or 1 and a process for its preparation and its use in the preparation of β-aryl-α-substituted hydroxyalkanoic acids is provided.

The compound of formula (Ih) where all other symbols are as defined earlier may be prepared by reacting a compound of formula (In)

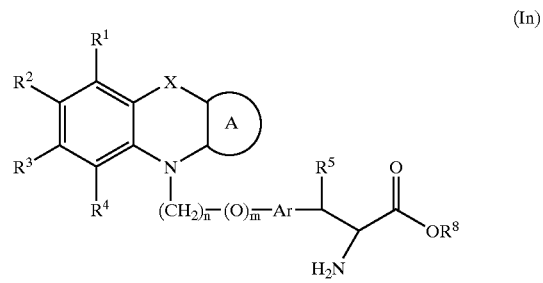

(In)

where $R^6$ is hydrogen atom and all other symbols are as defined earlier, with an appropriate diazotizing agent.

The diazotization reaction may be under conventional conditions. A suitable diazotizing agent is an alkyl nitrile, such as iso-amyl nitrile. The reaction may be carried out in presence of solvents such as THF, dioxane, ether, benzene and the like or a combination thereof. Temperature in the range of $-50°$ C. to $80°$ C. may be used. The reaction may be carried out in an inert atmosphere which may be maintained by using inert gases such as $N_2$, Ar or He. The duration of the reaction may range from 1 to 24 h, preferably, 1 to 12 h.

The compound of formula (In) may be prepared by a reaction between (IIIe) where all symbols are as defined earlier and a compound of formula (Io)

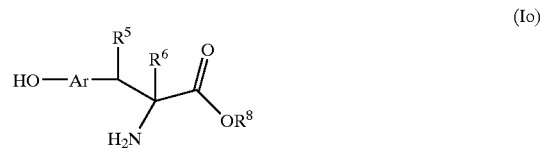

(Io)

where $R^6$ is hydrogen atom and all other symbols are as defined earlier.

The reaction of compound of formula (IIIe) where all symbols are as defined earlier and a compound of formula (Io) where all symbols are as defined earlier may be carried out in the presence of solvents such as THF, DMF, DMSO, DME and the like or mixtures thereof. The reaction may be carried out in an inert atmosphere which is maintained by using inert gases such as $N_2$, Ar or He. The reaction may be effected in the presence of a base such as $K_2CO_3$, $Na_2CO_3$ or NaH or mixtures thereof. Acetone may be used as a solvent when $K_2CO_3$ or $Na_2CO_3$ is used as a base. The reaction temperature may range from $20°$ C.–$120°$ C., preferably at a temperature in the range of $30°$ C.–$80°$ C. The duration of the reaction may range from 1 to 24 hours, preferably from 2 to 12 hours.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases such as diethanolamine, choline and the like; chiral bases like alkyl phenyl amine, phenyl glycinol and the like; natural aminoacids such as lysine arginine, guanidine, and the like, unnatural aminoacids such as D-isomers or substituted aminoacids; ammonium or substituted ammonium salts and aluminum salts may also be used. Alternatively, acid addition salts wherever applicable are prepared by treatment with acids such as hdyrochloric acid, hydrobromic acid, nitric acid, sulfuric acid, phosphoric acid, p-toluenesulphonic acid, methanesulfonic acid, acetic acid, citric acid, maleic acid salicyclic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxate etc. Mixtures of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) where $YR^9$ represents OH may be converted to a 1:1 mixture of diastereomeric amides by treating with chiral amines, aminoacids, aminoalcohols derived from aminoacids; conventional reaction conditions may be employed to convert acid into an amide, the diastereomers may be separated either by fractional crystallization or chromatography and the stereoisomers of compound of formula (I) may be prepared by hydrolyzing the pure diastereomeric amide.

Various polymorphs of compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The present invention provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates in combination with the usual pharmaceutically employed carriers, diluents and the like, useful for the treatment and/or prophylaxis of diseases such as hypertension, coronary heat disease, atherosclerosid, stroke, peripheral vascular diseases and related disorders. These compounds are useful for the treatment of familial hypercholesterolemia, hypertriglyceridemia, lowering of atherogenic lipoproteins, VLDL and LDL. The compounds of the present invention can e used for the treatment of certain renal diseases including glomerulonephritis, glomerulosclerosis, nephrotic syndrome, hypertensive nephrosclerosis, retinopathy, nephropathy. The compounds of general formula (I) are also useful for the treatment/prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders. These compounds may also be useful as aldose reductase inhibitors, for improving cognitivie functions in dementia, as inflammatory agents, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, xanthoma and for the treatment of cancer. The compounds of the present inventions are useful in the treatment and/or prophylaxis of the above said diseases in combination/concomittant with one or more HMG CoA reductase inhibitors, hypolipidemic/hypolipoproteinemic agents such as fibric acid derivatives, nicotinic acid, cholestyramine, colestipol, probucol or their combination. The compounds of the present invention in combination with HMG CoA reductase inhibitors, hypolipidemic/hypolipoproteinemic agents can be administered together or within such a period to act synergistically. The HMG CoA reducts inhibitors may be selected from those used for the treatment or prevention of hyperlipidemia such as lovastatin, provastatin, simvastatin, flavastatin, atorvastatin, cerivastatin and their analogs thereof. Suitable fibric acid derivative may be gemfibrozil, clofibrate, fenofibrate, ciprofibrate, benzafibrate and their analog thereof.

The present invention also provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates and one or more HMG CoA reductase inhibitors, hypolipidemic/hypolipoproteinemic agents such as fibric acid derivatives, nicotinic acid, cholestyramine, colestipol, probucol in combination with the usual pharmaceutically employed carriers, diluents and the like.

The pharmaceutical composition may be in the forms normally employed, such as tablets, capsules, powders, syrups, solutions, suspensions and the like, may contain falvourants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like.

The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as solutions of water-soluble pharmaceutically-acceptable acid addition salts or salts with base of the compounds. The injectable solutions prepared in this manner can then be administered intravenously, intraperiotoneally, subcutaneously, or intramuscularly, with intramuscular administration being preferred in humans.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

The invention is explained in detail in the examples given below which are provided by way of illustration only and therefore should not be construed to limit the scope of the invention.

PREPARATION 1

Ethyl (E/Z)-3-[4-benzyloxyphenyl]-2-ethoxypropenoate

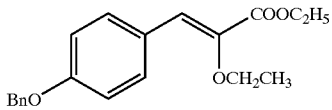

A solution of triethyl-2-ethoxyphosphonoacetate prepared by the method of Grell and Machleidt, *Annalen. Chemie,* 1996, 699, 53 (3.53 g, 13.2 mmol) in dry tetrahydrofuran (10 mL) was added slowly to a stirred ice cooled suspension of sodium hydride (60% dispersion of oil) (0.62 g, 25.94 mmol) in dry tetrahydrofuran (5 mL), under a nitrogen atmosphere. The mixture was stirred at 0° C. for 30 min. prior to the addition of a 4-benzyloxybenzaldehyde (2.5 g, 11.79 mmol) in dry tetrahydrofuran (20 mL). The mixture was allowed to warm up to room temperature and stirred at that temperature for further 20 h. The solvent was evaporated, water (100 mL) was added and extracted with ethyl acetate (2×75 mL). The combined organic extracts were washed with water (50 mL), brine (50 mL), dried ($Na_2SO_4$), filtered and the solvent was evaporated under reduced pressure. The residue was chromatographed over silica gel using a mixture of ethyl acetate and pet. ether (2:8) as an eluent to afford the title compound (3.84 g, quantitative) as an oil. $^1$H NMR of the product suggests a (76:24=Z/E) mixture of geometric isomers (R. A. Aitken and G. L. Thom, *Synthesis,* 1989, 958).

$^1$H NMR (CDCl$_3$, 200 MHz): δ 1.25–1.50 (complex, 6H), 3.85–4.03 (complex, 2H), 4.28 (q, J=7.0 Hz, 2H), 5.05, 5.09 (2s, 2H, benzyloxy CH$_2$), 6.08 (s, 0.24H, E isomer of olefinic proton), 6.85–6.90 (complex, 2H), 6.99 (s, 0.76H, Z isomer) 7.33–7.45 (complex, 5H), 7.75 (d, J=8.72 Hz, 2H).

PREPARATION 2

Methyl 3-[4-benzyloxyphenyl]-2-ethylpropanoate

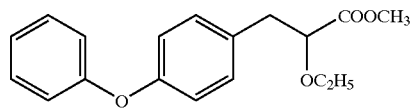

A mixture of ethyl (E/Z)-3-[4-benzyloxyphenyl]-2-ethoxypropanoate (3.84 g, 11.79 mmol obtained in the preparation 1) and magnesium turnings (5.09 g, 0.21 mol) in dry methanol (40 mL) was stirred at 25° C. for 1 h. Water (80 mL) was added and pH of solution was adjusted to 6.5–7.5 with 2N hydrochloric acid. The solution was extracted with ethyl acetate (3×75 mL). The organic layers were washed with water (50 mL), brine (50 mL) dried ($Na_2SO_4$) and filtered. The solvent was evaporated under reduced pressure to afford the title compound (3.7 g, quantitatively yield) as an oil.

$^1$H NMR (CDCl$_3$, 200 MHz): δ 1.16 (t, J=6.97 Hz, 3H), 2.95 (d, J=6.55 Hz, 2H), 3.30–3.38 (complex, 1H), 3.55–3.67 (complex, 1H), 3.69 (s, 3H), 3.99 (t, J=6.64 Hz, 1H), 5.04 (s, 2H), 6.89 (d, J=8.63 Hz, 2H), 7.15 (d, J=8.62 Hz, 2H), 7.31–7.41 (complex, 5H).

PREPARATION 3

Methyl 3-(4-hydroxyphenyl)-2-ethoxypropanoate

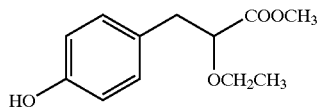

A suspension of methyl 3-[4-(benzyloxyphenyl)-2-ethoxypropanoate (3.7 g, 11.78 mmol; preparation 2) and 10% Pd-C (0.37 g) in ethyl acetate (50 mL) was stirred at 25° C. under 60 psi hydrogen pressure for 24 h. The catalyst was filtered and the solvent was evaporated under reduced pressure. The residue was chromatographed over silica gel using a mixture of ethyl acetate and pet. ether (2:8) and an eluent to afford the title compound (2.2 g, 84%) as an oil.

$^1$H NMR (CDCl$_3$, 200 MHz): δ 1.21 (t, J=6.97 Hz, 3H), 2.99 (d, J=6.37 Hz, 2H), 3.32–3.49 (complex, 1H), 3.57–3.65 (complex, 1H), 3.76 (s, 3H), 4.05 (t, J=6.64 Hz, 1H), 5.19–5.40 (bs, 1H, D$_2$O exchangeable), 6.80 (d, J=8.44 Hz, 2H), 7.14 (d, J=8.39 Hz, 2H).

PREPARATION 4

Ethyl 3-[4-hydroxyphenyl]-2-ethoxypropanoate

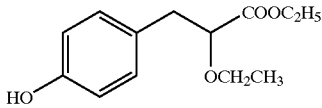

The title compound (1.73 g, 61%) was prepared as a colourless oil from ethyl (E/Z)-3-[4-benzyloxyphenyl]-2-ethoxypropenote (3.85 g, 11.80 mmol) obtained in preparation 1 by hydrogenation procedure described in preparation 3.

$^1$H NMR (CDCl$_3$, 200 MHz): δ 1.12–1.29 (complex, 6H), 2.93 (d, J=6.55 Hz, 2H), 3.28–3.45 (complex, 1H), 3.51–3.68 (complex, 1H), 3.98 (t, J=6.55 Hz, 1H), 4.16 (q, J=7.15 Hz, 2H), 5.40 (s, 1H, D$_2$O exchangeable), 6.73 (d, J=8.39 Hz, 2H), 7.08 (d, J=8.53 Hz, 2H).

PREPARATION 5

Ethyl 3-[4-benzyloxyphenyl]-2-butoxypropanoate

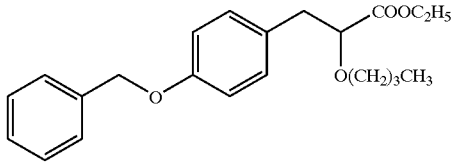

A solution of ethyl 3-[4-benzyloxyphenyl)-2-hydroxypropanoate (5.0 g, 16.6 mmol) (prepared in a similar manner as described in Ref: WO95/18125) in dry dimethyl formamide (5 mL) was added to a suspension of sodium hydride (0.1 g, 41.6 mmol) (60% dispersion in oil) in dry dimethyl formamide (3 mL) at 0° C. and stirring was continued for further 1 h. To the above reaction mixture n-butyl bromide (3.4 g, 24.0 mmol) was added at 0° C. and stirring was continued for 10 h at ca. 25° C. Water (30 mL) was added and extracted with ethyl acetate 2×50 mL). The combined ethyl acetate layer was washed with water (50 mL), brine (25 mL), dried (Na$_2$SO$_4$), filtered and the solvent was evaporated. The residue was chromatographed over silica gel using a mixture of ethyl acetate and the pet. ether (1:9) as an eluent to afford the title compound (0.7 g, 20%) as an oil.

$^1$H NMR (CDCl$_3$, 200 MHz): δ 0.85 (t, J=7.38 Hz, 3H), 1.18–1.40 (complex, 5H), 1.49–1.58 (complex, 2H), 2.94 (d, J=6.74 Hz, 2H), 3.20–3.33 (complex, 1H), 3.46–3.61 (complex, 1H), 3.94 (t, J=6.37 Hz, 1H), 4.16 (q, J=7.0 Hz, 2H), 5.04 (s, 2H), 6.89 (d, J=8.5 Hz, 2H), 7.15 (d, J=8.48 Hz, 2H), 7.30–7.44 (complex, 5H).

PREPARATION 6

Ethyl 3-[4-hydroxyphenyl]-2-butoxypropanoate

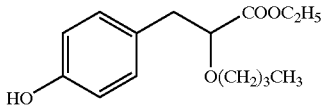

The title compound (0.475 g, 75%) was prepared as an oil from ethyl 3-[4-benzyloxyphenyl)-2-butoxypropanoate (0.85 g, 2.38 mmol) obtained in preparation 8 by an analogous procedure to that described in preparation 3.

$^1$H NMR (CDCl$_3$, 200 MHz): δ 0.85 (t, J=7.24 Hz, 3H), 1.19–1.38 (complex, 5H), 1.44–1.58 (complex, 2H), 2.94 (d, J=6.55 Hz, 2H), 3.21–3.32 (complex, 1H), 3.49–3.62 (complex, 1H), 3.94 (t, J=6.88 Hz, 1H), 4.16 (q, J=7.1 Hz, 2H), 4.99 (s, 1H, D$_2$O exchangeable), 6.73 (d, J=8.53 Hz, 2H), 7.09 (d, J=8.44 Hz, 2H).

PREPARATION 7

Ethyl 3-[4-benzyloxyphenyl]-2-hexyloxypropanoate

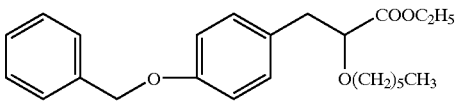

The title compound (1.2 g, 22%) was prepared as an oil from ethyl 3-(4-benzyloxyphenyl)-2-hydroxypropanoate (4.2 g, 14.0 mmol) and 1-bromohexane (3.4 g, 21.0 mmol) by an analogous procedure to that described in preparation 5.

$^1$H NMR (CDCl$_3$, 200 MHz): δ 0.86 (t, J=5.9 Hz, 3H), 1.18–1.37 (complex, 7H), 1.45–1.66 (complex, 4H), 2.94 (d, J=6.55 Hz, 2H), 3.22–3.33 (complex, 1H), 3.52–3.64 (complex 1H), 3.94 (t, J=6.9 Hz, 1H), 4.16 (q, J=7.06 Hz, 2H), 5.03 (s, 2H), 6.89 (d, J=8.63 Hz, 2H), 7.15 (d, J=8.63 Hz, 2H), 7.31–7.44 (complex, 5H).

PREPARATION 8

Ethyl 3-[4-hydroxyphenyl]-2-hexyloxypropanoate

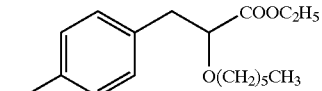

The title compound (0.7 g, 76%) was prepared as an oil from ethyl 3-[4-benzyloxyphenyl)-2-hexyloxypropanoate (1.2 g, 3.1 mmol) obtained in preparation 7 by an analogous procedure to that described in preparation 3.

$^1$H NMR (CDCl$_3$, 200 MHz): δ 0.85 (t, J=5.81 Hz, 3H), 1.19–1.39 (complex, 7H), 1.48–1.68 (complex, 4H), 2.92 (d, J=6.74 Hz, 2H), 3.18–3.39 (complex, 1H), 3.48–3.62 (complex, 1H), 3.93 (t, J=7.0 Hz, 1H), 4.16 (q, J=7.06 Hz, 2H), 4.85 (s, 1H, D$_2$O exchangeable), 6.73 (d, J=8.53 Hz, 2H), 7.10 (d, J=8.31 Hz, 2H).

PREPARATION 9

Ethyl (E/Z)-3-[4-(2-bromoethoxy)phenyl]-2-ethoxypropenoate

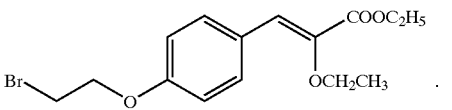

The title compound (4.0 g, 66%) was prepared as an oil in 45:55 ratio of E:Z isomers (as measured by $^1$H NMR) from 4-(2-bromoethoxy)benzaldehyde (4.0 g, 17.4 mmol) and triethyl-2-ethoxyphosphonoacetate (5.61 g, 20.89 mmol) by an analogous procedure to that described in preparation 1.

$^1$H NMR (CDCl$_3$, 200 MHz): δ 1.17 and 1.42 (6H, E and Z triplets, isomeric —OCH$_2$CH$_3$ and OCH$_2$—CH$_3$), 3.62–3.72 (complex, 2H), 3.90–4.28 (complex, 2H), 4.30–4.37 (complex, 4H, 6.09 (s, 0.45H, olefinic proton of E isomers), 6.85 and 6.92 (2H, d and d, J=8.67 Hz and 8.7 Hz), 6.98 (s, 0.55H, Z isomer of olefinic proton), 7.16 and 7.78 (d and d, combined 2H, J=8.63 Hz and 8.72 Hz).

PREPARATION 10

Ethyl 3-[4-(2-bromoethoxy)phenyl]-2-ethoxypropanoate

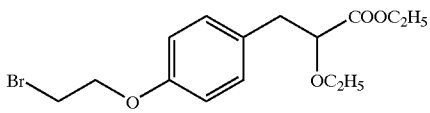

The title compound (4.0 g, 80%) was prepared as colorless oil from ethyl (E/Z)-3-[4-(2-bromoethoxy)phenyl]-2-ethoxypropenoate (5.0 g, 14.5 mmol) obtained in preparation 9 using H$_2$/10% Pd-C (4 g) in dioxane as a solvent by an analogous procedure to that described in preparation 3.

$^1$H NMR (CDCl$_3$, 200 MHz): δ 1.12–1.30 (complex, 6H), 2.95 (d, J=6.64 Hz, 2H), 3.25–3.45 (complex, 1H), 3.56–3.68 (complex, 3H), 3.96 (t, J=6.65 Hz, 1H), 4.16 (q, J=7.1 Hz, 2H), 4.27 (t, J=6.3 Hz, 2H), 6.81 (d, J=8.67 Hz, 2H), 7.16 (d, J=8.63 Hz, 2H).

EXAMPLE 1

Ethyl (E/Z)-3-[4-[2-(Phenothiazin-10-yl)ethoxy]phenyl]-2-ethoxypropenoate

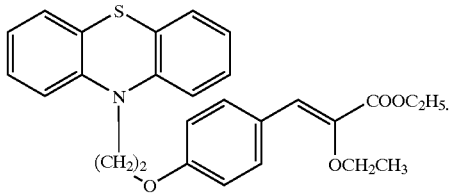

The title compound was obtained as 1:1 E:Z isomers (1.46 g, quantitative) as a syrupy liquid from 4-[2-(phenothiazin-10-yl)ethoxy]benzaldehyde (1.08 g, 3.11 mmol) and triethyl-2-ethoxyphosphonoacetate (W. Grell & H. Machleidt, Annalen chemie, 1966, 699, 53) (1.0 g, 3.73 mmol) by an analogous procedure to that described in preparation 1.

$^1$H NMR (CDCl$_3$, 200 MHz): δ 1.15–1.43 (complex, 6H), 3.89–4.03 (complex, 2H), 4.11–4.17 (complex, 2H), 4.30, 4.33 (complex, 4H, —CH$_2$CH$_2$-singlets), 6.07 (s, 0.5H, olefinic proton of E isomer), 6.80–7.10 (complex, 6.5H), 7.14–7.20 (complex, 4H), 7.73 (d, J=8.39 Hz, 2H).

EXAMPLE 2

Ethyl (E/Z)-3-[2-phenotiazin-10-yl)methylbenzofuran-5-yl]-2-ethoxypropenoate

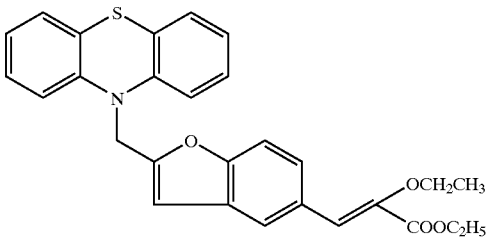

The title compound was obtained as E:Z isomers (38:62) (as measured by $^1$H NMR) (1.5 g, 100%) as a colourless liquid from 5-formyl-2-(phenothiazin-10-yl) methylbenzofuran (1.14 g, 3.2 mmol) by a procedure similar to that described for preparation 1.

$^1$H NMR (CDCl$_3$, 200 MHz): δ 1.23–1.45 (complex, 6H), 3.55–3.78 (complex, 1H), 3.88–4.19 (complex, 1H), 4.22–4.35 (complex, 2H), 5.14 (s, 2H), 6.18 (s, 0.38H, olefinic proton of E isomer) 6.47 and 6.54 (combined,1H), 6.78–7.12 (complex, 8.62H), 7.37–7.48 (complex, 1H), 7.71 (d, J=7.57 Hz, 1H), 7.95 (s, 1H).

EXAMPLE 3

Ethyl (E/Z)-3-[4-[2-(phenoxazin-10-yl)ethoxy]phenyl]-2-ethoxypropenoate

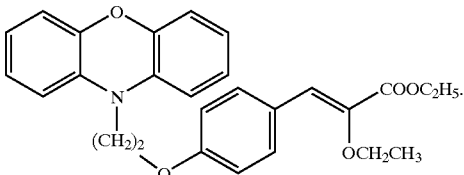

The title compound (14.4 g, 76%) was obtained as E:Z isomer (36:64) (as measured by $^1$H NMR) as a white solid from 4-[2-(phenoxazin-10-yl)ethoxy]benzaldehyde (14.0 g, 42.3 mmol) by an analogous procedure to that described for preparation 1, mp: 110–112° C.

$^1$H NMR (CDCl$_3$, 200 MHz): δ 1.16 and 1.38 (combined, 6H, isomeric —OCH$_2$CH$_3$ triplet signals), 3.89–4.05 (complex, 4H), 4.14–4.31 (complex, 4H), 6.06 (s, 0.36H, olefinic proton of E isomer), 6.66–6.95 (complex, 10.64H), 7.75 (d, J=8.76 Hz, 2H).

EXAMPLE 4

(±) Methyl 3-[4-[2-(phenothiazin-10-yl)ethoxy]phenyl]-2-ethoxypropanoate

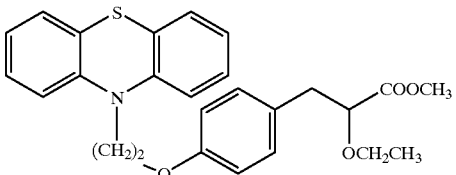

The title compound (1.3 g, 94%) was prepared as a gummy liquid from ethyl (E/Z)-3-[4-[2-(phenothiazin-10- yl)ethoxy]phenyl]-2-ethoxypropenoate (1.43 g, 3.10 mmol) obtained in example 1 by an analogous procedure to that described in preparation 2.

$^1$H NMR (CDCl$_3$, 200 MHz): δ 1.15 (t, J=7.00 Hz, 3H), 2.93 (d, J=6.64 Hz, 2H), 3.33–3.42 (complex, 1H), 3.52–3.63 (complex, 1H), 3.69 (s, 3H), 3.97 (t, J=6.20 Hz, 1H), 4.29 (s, 4H), 6.81 (d, J=8.62 Hz, 2H), 6.92–6.96 (complex, 4H), 7.12–7.22 (complex, 6H).

EXAMPLE 5

(±) Methyl 3-[2-(phenothiazin-10-yl) methylbenzofuran-5-yl]-2-ethoxypropanoate

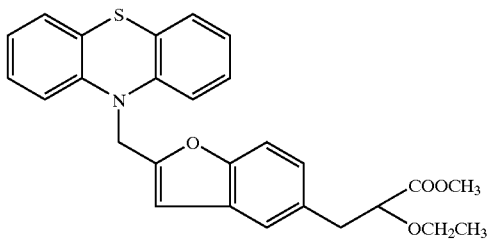

The title compound (1.0 g, 68%) was prepared as a gum, from ethyl (E/Z)-3-[2-(phenothiazin-10-yl) methylbenzofuran-5-yl]-2-ethoxypropenoate (1.5 g, 3.0 mmol) obtained in example 2 by an analogous procedure to that described in preparation 2.

$^1$H NMR (CDCl$_3$, 200 MHz): δ 1.16 (t, J=7.00 Hz, 3H), 3.07 (d, J=6.55 Hz, 2H), 3.30–3.49 (complex, 1H), 3.56–3.68 (complex, 1H), 3.70 (s,3H), 4.05 (t, J=6.3 Hz, 1H), 5.13 (s, 2H), 6.48 (s, 1H), 6.79–7.48 (complex, 11H).

EXAMPLE 6

(±) Methyl 3-[4-[2-(phenoxazin-10-yl)ethoxy] phenyl]-2-ethoxypropanoate

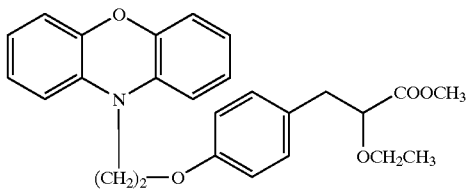

Method A

The title compound (0.68 g, 52%) was prepared as a white solid, from ethyl (E/Z)-3-[4-[2-(phenoxazin-10-yl)ethoxy] phenyl]-2-ethoxypropenoate (1.3 g, 2.9 mmol) obtained in example 3 by a procedure similar to that described in preparation 2, mp: 88–90° C.

Method B

A mixture of 2-(phenoxazin-10-yl)ethyl methanesulfonate (1.75 g, 5.0 mmol), methyl 3-(4-hydroxyphenyl)-2-ethoxypropanoate (1.5 g, 0.68 mmol) obtained in preparation 3 and potassium carbonate (3.16 g) in dry dimethylformamide (20 mL) was stirred for 12 h at 80° C. The reaction mixture was cooled to room temperature (ca. 25° C.). Water (30 mL) was added and extracted with ethyl acetate (2×50 mL). The combined organic extracts were washed with water (50 mL), dried (Na$_2$SO$_4$) and evaporated. The residue was chromatographed using a mixture of ethyl acetate and pet. ether (1:9) to afford the title compound (1.15 g, 47%) as a white solid, mp: 89–90° C. $^1$H NMR data matches with the desired product (see above).

$^1$H NMR (CDCl$_3$, 200 MHz): δ 1.16 (t, J=6.92 Hz, 3H), 2.96 (d, J=6.64 Hz, 2H), 3.22–3.40 (complex, 1H), 3.51–3.66 (complex, 1H), 3.68 (s, 3H), 4.00 (t, J=7.0 Hz, 1H), 4.18 (complex, 4H), 6.55–6.89 (complex, 10H), 7.12 (d, J=8.63 Hz, 2H).

EXAMPLE 7

(±) Ethyl 3-[4-[2-(phenoxazin-10-yl)ethoxy] phenyl]-2-ethoxypropanoate

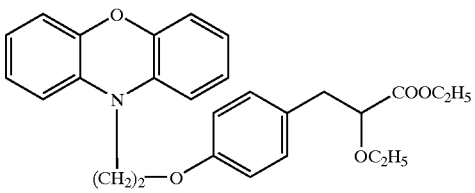

Method A

To a solution ethyl (E/Z)-3-[4-[2-(phenoxazin-10-yl) ethoxy]phenyl]-2-ethoxypropenoate (1.0 g, 2.24 mmol) obtained in example 3 in dioxane (50 mL) was added 10% Pd-C (0.25 g) and stirred at 25° C. under 60 psi hydrogen pressure for 24 h. At the end of this time reaction mixture was filtered and the solvent was evaporated under reduced pressure. The residue was triturated with pet. ether to afford the title compound (0.96 g, 96%) as a white solid, mp: 51–53° C.

$^1$H NMR (CDCl$_3$, 200 MHz): δ 1.12–1.27 (complex, 6H), 2.94 (d, J=6.31 Hz, 2H), 3.26–3.41 (complex, 1H), 3.52–3.75 (complex, 1H), 3.96 (t, J=6.64 Hz, 2H), 4.10–4.28 (complex, 5H), 6.55–6.92 (complex, 10H), 7.16 (d, J=8.39 Hz, 2H).

Method B

The title compound (0.55 g, 75%) was prepared as a white solid from 2-(phenoxazin-10-yl)ethyl methanesulfonate (0.5 g, 1.63 mmol) and ethyl 3-(4-hydroxyphenyl)-2-ethoxypropanoate (0.46 g, 1.9 mmol) obtained in preparation 4 by a procedure similar to that described in example 6 (Method B). mp: 52–53° C. The $^1$H NMR data matches with the desired product (see above).

Method C

To a suspension of sodium hydride (60% dispersion in oil) (0.098 g, 4.0 mmol) in dry dimethyl formamide (3 mL) was added a solution of phenoxazine (0.3 g, 1.6 mmol) in dry dimethyl formamide (5 mL) at 0° C. under nitrogen atmosphere and stirred for 30 min at ca. 25° C. To the above reaction mixture a solution of ethyl 3-[4-(2-bromoethoxy) phenyl]-2-ethoxypropanoate (0.85 g, 2.4 mmol) obtained in preparation 10 in dry dimethyl formamide (5 mL) at 0° C. and stirring was continued for a further 10 h at ca. 25° C. Water (40 mL) was added and extracted with ethyl acetate (2×30 mL). The combined organic extracts were washed with water (25 mL), brine (25 mL), dried (Na$_2$SO$_4$), filtered and evaporated. The residue was chromatographed over silica gel using a mixture of ethyl acetate and pet. ether (1:9) as an eluent to afford the title compound (0.3 g, 40%) as a colourless solid. mp: 52–53° C. The $^1$H NMR data matches with the desired product (see above).

EXAMPLE 8

(±) Ethyl 3-[4-[2-(phenoxazin-10-yl)ethoxy]phenyl]-2-hydroxypropanoate

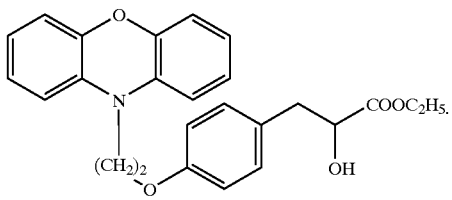

The title compound (1.06 g, 43%) was prepared as a pale yellow liquid from (2-phenoxazin-10-yl)ethyl methanesulfonate (1.8 g, 5.9 mmol) and ethyl 3-(4-hydroxyphenyl)-2-hydroxy propanoate (1.36 g, 6.49 mmol) by an analogous procedure to that described in example 6 (Method B).

$^1$H NMR (CDCl$_3$, 200 MHz): δ 1.29 (t, J=6.96 Hz, 3H), 2.85–3.12 (complex, 2H), 3.92 (bs, 2H), 4.10–4.27 (complex, 4H), 4.39 (t, J=6.1 Hz, 1H), 6.68–6.89 (complex, 10 H), 7.13 (d, J=8.39 Hz, 2H). OH proton is too broad to observe.

EXAMPLE 9

(±) Ethyl 3-[4-[2-(phenoxazin-10-yl)ethoxy]phenyl]-2-butoxypropanoate

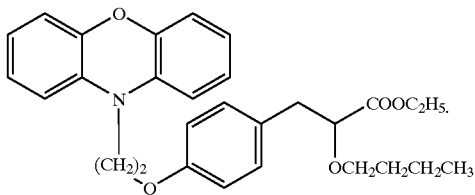

The title compound (0.25 g, 53%) was prepared as a colourless liquid from 2-(phenoxazin-10-yl)ethyl methanesulfonate (0.3 g, 0.98 mmol) and ethyl 3-(4-hydroxyphenyl)-2-butoxy propanoate (0.26 g, 0.97 mmol) obtained in preparation 6 by an analogous procedure to that described in example 6 (Method B).

$^1$H NMR (CDCl$_3$, 200 MHz): δ 0.92 (t, J=6.40 Hz, 3H), 1.21–1.39 (complex, 5H), 1.45–1.58 (complex, 2H), 2.94 (d, J=6.32 Hz, 2H), 3.24–3.31 (complex, 1H), 3.50–3.57 (complex, 1H), 3.94 (t, J=6.13 Hz, 1H), 4.13–4.23 (complex, 6H), 6.61–6.84 (complex, 10 H), 7.16 (d, J=8.3 Hz, 2H).

EXAMPLE 10

(±) Ethyl 3-[4-[2-(phenoxazin-10-yl)ethoxy]phenyl]-2-hexyloxypropanoate

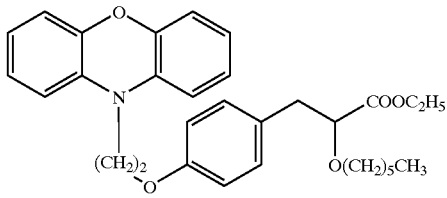

The title compound (0.52 g, 53%) was prepared as a pale yellow oil from 2-(phenoxazin-10-yl)ethyl methanesulfonate (0.6 g and 1.97 mmol) and ethyl 3-(4-hydroxyphenyl)-2-hexyloxypropanoate (0.70 g, 2.4 mmol) obtained in preparation 8 by an analogous procedure to that described in example 6 (Method B).

$^1$H NMR (CDCl$_3$, 200 MHz): δ 0.85 (t, J=6.00 Hz, 3H), 1.20–1.27 (complex, 7H), 1.48–1.57 (complex, 4H), 2.94 (d, J=6.00 Hz, 2H), 3.21–3.30 (complex, 1H), 3.52–3.56 (complex, 1H), 3.90–3.99 (complex, 3H), 4.13–4.22 (complex, 4H), 6.60–6.83 (complex, 10 H), 7.15 (d, J=8.62 Hz, 2H).

EXAMPLE 11

(±) 3-[4-[2-(Phenothiazin-10-yl)ethoxy]phenyl]-2-ethoxypropanoic acid

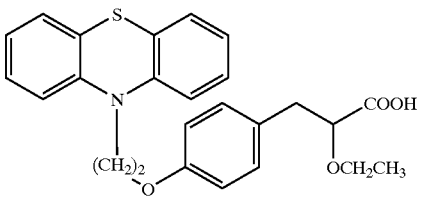

To a solution of (±) methyl 3-[4-[2-(phenothiazin-10-yl)ethoxy]phenyl]-2-ethoxypropanoate (7.5 g, 16.70 mmol) obtained in example 4 in methanol (50 mL) was added aqueous 10% sodium hydroxide (20 mL). The reaction mixture was stirred at ca. 25° C. for 3 h. The solvent was removed under reduced pressure and the residue was acidified with 2 N hydrochloric acid, extracted with ethyl acetate (2×100 mL). The combined ethyl acetate extract was washed with water (50 mL), brine (50 mL), dried (Na$_2$SO$_4$), filtered and solvent was evaporated under reduced pressure. The residue was chromatographed over silica gel using a mixture of dichloromethane and methanol (9:1) as an eluent to afford the title compound (6.0 g, 83%) as a white solid. mp: 79–82° C.

$^1$H NMR (CDCl$_3$, 200 MHz): δ 1.18 (t, J=6.80 Hz, 3H), 2.88–3.11 (complex, 2H), 3.39–3.64 (complex, 2H), 4.06 (dd, J=9.2 and 4.3 Hz, 1H), 4.30 (s, 4H), 5.30–5.98 (bs, 1H, D$_2$O exchangeable), 6.80–7.02 (complex, 6H), 7.12–7.21 (complex, 6H).

EXAMPLE 12

(±) 3-[4-[2-(Phenothiazin-10-yl)ethoxy]phenyl]-2-ethoxypropanoic acid, sodium salt

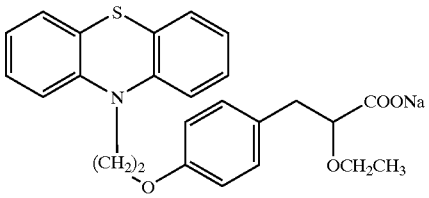

A mixture of (±) 3-[4-[2-(phenothiazin-10-yl)ethoxy]phenyl]-2-ethoxypropanoic acid (0.3 g, 0.689 mmol) obtained in example 11 and sodium methoxide (0.041 g, 0.758 mmol) in methanol (5 mL) was stirred at ca. 25° C. for 2 h. The solvent was removed under reduced pressure and the residue was triturated with dry ether (3×10 mL). The separated solid was filtered, washed with dry ether (2×5 mL)

and dried over P$_2$O$_5$ under reduced pressure to afford the title compound (0.25 g, 89%) as a white solid. mp: 188–191° C.

1H NMR (DMSO-d$_6$, 200 MHz): δ 1.04 (t, J=6.90 Hz, 3H), 2.71–2.89 (complex, 1H), 2.90–3.06 (complex, 1H), 3.16–3.30 (complex, 1H), 3.36–3.54 (complex, 1H), 3.88–3.91 (complex, 1H), 4.21 (s, 4H), 6.72 (d, J=8.3 Hz, 2H), 6.89–6.99 (complex, 4H), 7.05–7.21 (complex, 6H).

EXAMPLE 13

(±) 3-[2-(Phenothiazin-10-yl)methylbenzofuran-5-yl]-2-ethoxypropanoic acid

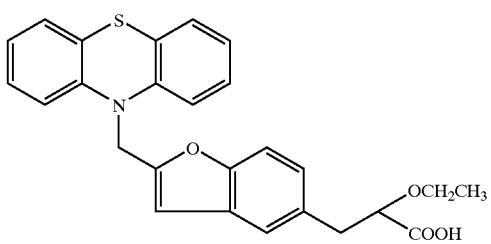

The title compound (0.8 g, 83%) was prepared as a white solid from (±) methyl 3-[2-(phenothiazin-10-yl) methylbenzofuran-5-yl]-2-ethoxypropanoate (1.0 g, 2.0 mmol) obtained in example 5 by a procedure analogous to that described in example 11. mp: 120–121° C. COOH proton is too broad to observe.

$^1$H NMR (CDCl$_3$, 200 MHz): δ 1.15 (t, J=6.95 Hz, 3H), 3.00–3.26 (complex, 2H), 3.40–3.68 (complex, 2H), 4.08 (t, J=4.47 Hz, 1H), 5.11 (s, 2H), 6.46 (s, 1H), 6.77–7.40 (complex, 11H).

EXAMPLE 14

(±) 3-[2-(Phenothiazin-10-yl)methylbenzofuran-5-yl]-2-ethoxypropanoic acid, sodium salt

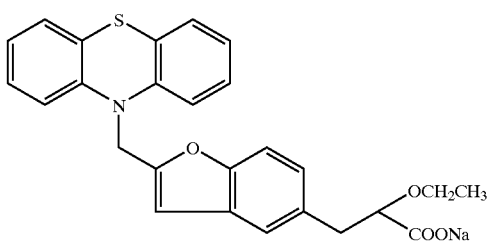

The title compound (0.12 g, 67%) was prepared as a white solid from (±) 3-[2-(phenothiazin-10-yl)methylbenzofuran-5-yl]-2-ethoxypropanoic acid (0.16 g, 0.38 mmol) obtained in example 13 by a procedure analogous to that described for example 12. mp: 258–261° C.

$^1$H NMR (CDCl$_3$, 200 MHz): δ 0.95 (t, J=6.97 Hz, 3H), 2.62–2.80 (complex, 1H), 2.89–3.02 (complex, 1H), 3.06–3.18 (complex, 1H), 3.22–3.31 (complex, 1H), 3.50–3.61 (complex, 1H), 5.25 (s, 2H), 6.64 (s, 1H), 6.90–7.39 (complex, 1H).

EXAMPLE 15

(±) 3-[4-[2-(Phenoxazin-10-yl)ethoxy]phenyl]-2-ethoxypropanoic acid

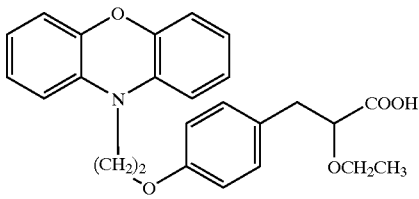

The title compound (5.4 g, 77%) was prepared as a white solid from (±) methyl 3-[4-[2-(phenoxazin-10-yl)ethoxy]phenyl]-2-ethoxypropanoate (7.5 g, 16.8 mmol) obtained in example 6 by a procedure similar to that described in example 11. mp: 90–92° C.

$^1$H NMR (CDCl$_3$, 200 MHz): δ 1.19 (t, J=7.00 Hz, 3H), 2.90–3.18 (complex, 2H), 3.41–3.62 (complex, 2H), 3.90–4.10 (complex, 3H), 4.18 (t, J=6.20 Hz, 2H), 6.58–6.89 (complex, 10H), 7.16 (d, J=8.40 Hz, 2H). COOH proton is too broad to observe.

EXAMPLE 16

(±) 3-[4-[2-(Phenoxazin-10-yl)ethoxy]phenyl]-2-ethoxypropanoic acid, sodium salt

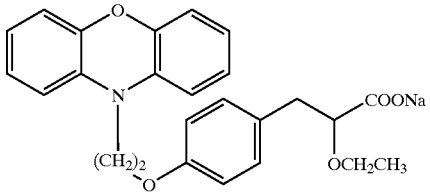

The title compound (0.27 g, 85%) was prepared as a white solid from (±) 3-[4-[2-(phenoxazin-10-yl)ethoxy]phenyl]-2-ethoxypropanoic acid (0.3 g, 0.72 mmol) obtained in example 15 by an analogous procedure to that described in example 12. mp: 194–202° C.

$^1$H NMR (CDCl$_3$, 200 Mhz): δ 0.92 (t, J=6.97 Hz, 3H), 2.65–2.82 (complex, 1H), 2.96–3.14 (complex, 2H), 3.31–3.41 (complex, 1H), 3.70–3.90 (complex, 3H) 3.94–4.04 (complex, 2H), 6.47–6.74 (complex, 10 H), 7.05 (d, J=8.30 Hz, 2H).

EXAMPLE 17

(±) 3-[4-[2-(Phenoxazin-10-yl)ethoxy]phenyl]-2-hydroxypropanoic acid

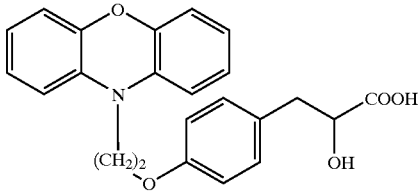

The title compound (0.40 g, 72%) was prepared as a brown liquid from (±) ethyl 3-[4-[2-(phenoxazin-10-yl)

ethoxy]phenyl]-2-hydroxypropanoate (0.6 g, 1.43 mmol) obtained in example 8 by an analogous procedure to that described in example 11.

$^1$H NMR (CDCl$_3$, 200 MHz) δ: 2.75 (bs, 1H, D$_2$O exchangeable), 2.86–3.23 (complex, 2H), 3.85 (t, J=6.0 Hz, 2H), 4.18 (t, J=5.90 Hz, 2H), 4.47 (complex, 1H), 6.58–6.89 (complex, 10H), 7.17 (d, J=8.63 Hz, 2H). COOH proton is too broad to observe.

EXAMPLE 18

(±) 3-[4-[2-(Phenoxazin-10-yl)ethoxy]phenyl]-2-butoxypropanoic acid

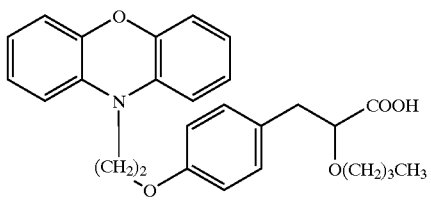

The title compound (0.13 g, 69%) was prepared as a cream coloured solid from (±) ethyl 3-[4-[2-(phenoxazin-10-yl)ethoxy]phenyl]-2-butoxypropanoate (0.2 g, 0.42 mmol) obtained in example 9 by an analogous procedure to that described in example 11. mp: 84–88° C.

$^1$H NMR (CDCl$_3$, 200 MHz): δ 0.88 (t, J=7.50 Hz, 3H), 1.26–1.47 (complex, 2H), 1.47–1.66 (complex, 2H), 2.87–3.16 (complex, 2H), 3.35–3.58 (complex, 2H), 3.88–4.08 (complex, 3H), 4.15 (t, J=6.4 Hz, 2H), 6.65–6.86 (complex, 10H), 7.15 (d, J=8.63 Hz, 2H), COOH proton is too broad to observe.

EXAMPLE 19

(±) 3-[4-[2-(Phenoxazin-10-yl)ethoxy]phenyl]-2-butoxypropanoic acid, sodium salt

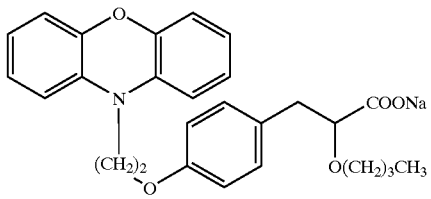

The title compound (0.07 g, 83%) was prepared as a cream coloured hygroscopic solid from (±) 3-[4-[2-(phenoxazin-10-yl)ethoxy]phenyl]-2-butoxypropanoic acid (0.08 g, 0.178 mmol) obtained in example 18 by a procedure similar to that described in example 12.

$^1$H NMR (DMSO-d$_6$, 200 MHz), δ 0.78 (t, J=7.28 Hz, 3H), 1.19–1.523(complex, 4H), 2.72–3.02 (complex, 2H), 3.45–3.67 (complex, 2H), 4.01 (bs, 3H), 4.18 (bs, 2H), 6.61–6.89 (complex, 8H), 7.10–7.24 (complex, 4H).

EXAMPLE 20

(±) 3-[4-[2-(Phenoxazin-10-yl)ethoxy]phenyl]-2-hexyloxypropanoic acid

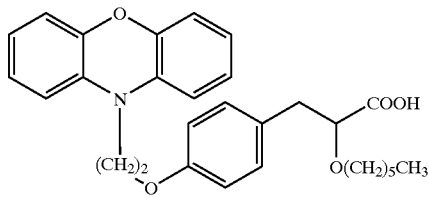

The title compound (0.10 g, 23%) was obtained as a syrupy liquid from (±) ethyl 3-[4-[2-(phenoxazin-10-yl) ethoxy]phenyl]-2-hexyloxypropanoate (0.46 g, 0.86 mmol) obtained in example 10 by an analogous procedure to that described in example 11.

$^1$H NMR (CDCl$_3$, 200 MHz): δ 0.86 (t, J=6.00 Hz, 3H), 1.18–1.30 (complex, 4H), 1.42–1.80 (complex, 4H), 2.88–3.18 (complex, 2H), 3.32–3.60 (complex, 2H), 3.89–4.09 (complex, 3H), 4.16 (t, J=6.0 Hz, 2H), 6.58–6.89 (complex, 10H), 7.14 (d, J=8.63 Hz, 2H). COOH is too broad to observe.

EXAMPLE 21

[(2R)-N(1S)]-3-[4-[2-(Phenoxazin-10-yl)ethoxy] phenyl]-2-ethoxy-N-(2-hydroxy-1-phenylethyl) propanamide (21a)

21a

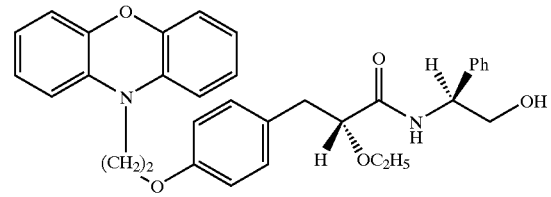

[(2S)-N(1S)]-3-[4-[2-(phenoxazin-10-yl)ethoxy] phenyl]-2-ethoxy-N-(2-hydroxy-1-phenylethyl) propanamide (21b)

21b

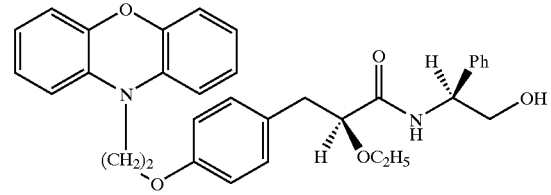

To an ice cooled solution of (±)-3-[4-[2-(phenoxazin-10-yl)-ethoxy]phenyl]-2-ethoxypropanoic acid (1.2 g, 2.9 mmol) obtained in example 15 and triethylamine (0.48 g, 5.8 mmol) in dry dichloromethane (25 mL) was added pivaloyl chloride (0.38 g, 3.19 mmol) and stirred for 30 min at 0° C. A mixture of (S)-2-phenylglycinol (0.39 g, 2.9 mmol) and triethylamine (0.58 g, 5.8 mmol) in dichloromethane (20 mL) was added to the above reaction mixture at 0° C. and stirring was continued for further 2 h at 25° C. Water (50 mL) was added and extracted with dichloromethane (2×50 mL). The organic extracts were washed with water (2×25 mL), brine (25 mL), dried (Na$_2$SO$_4$) and evaporated. The residue was chromatographed over silica gel using a gradient of 40–60% ethyl acetate in pet. ether as an eluent to afford firstly a diastereomer tentatively assigned as [2R, N(1S)]-3-[4-[2-(phenoxazin-10-yl)ethoxy]phenyl]-2-ethoxy-N-(2-hydroxy-1-phenylethyl)propanamide (0.55 g, 35%) (21 a) followed by [2S-N(1S)-3-[4-[2-(phenoxazin-10-yl)ethoxy]phenyl]-2-ethoxy-N-(2-hydroxy-1-phenylethyl) propanamide (0.5 g, 32%) (21b).

21a: mp: 126–128° C.

$[\alpha]_D^{25}$=+24.6 (c=1.0%, CHCl$_3$).

$^1$H NMR (CDCl$_3$, 200 MHz): δ 1.16 (t, J=7.20 Hz, 3H), 2.50 (bs, 1H, D$_2$O exchnageable), 2.92–3.20 (complex, 2H), 3.52 (q, J=7.05 Hz, 2H), 3.72 (bs, 2H), 3.99 (complex, 3H), 4.21 (t, J=6.64 Hz, 2H), 4.98–5.01 (complex, 1H), 6.64–6.70 (complex, 5H), 6.73–6.89 (complex, 4H), 7.03 (d, J=7.15 Hz, 1H), 7.18–7.29 (complex, 4H), (J=7.32–7.39 complex, 3H). CONH is too broad to observe.

21b: mp: 139–141° C.

$[\alpha]_D^{25}$=−13.3 (c, 1.00% CHCl$_3$)

$^1$H NMR (CDCl$_3$, 200 MHz); δ 1.18 (t, J=6.96 Hz, 3H), 2.05 (bs, 1H, D2O exchangeable), 2.80–3.14 (complex, 2H), 3.54 (q, J=7.00 Hz, 2H), 3.85 (bs, 2H), 3.97 (complex, 3H), 4.41 (t, J=6.23 Hz, 2H), 4.92–5.01 (complex, 1H), 6.62–6.85 (complex, 9H), 7.02–7.20 (complex, 5H), 7.26–7.30 (complex, 3H), CONH is too broad to observe.

EXAMPLE 22

(+) 3-[4-[2-(Phenoxazin-10-yl)ethoxy]phenyl]-2-ethoxypropanoic acid:

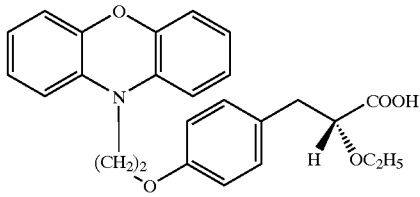

A solution of [2R, diastereomer, N(1S)]-3-[4-[2-(phenoxazin-10-yl)ethoxy]phenyl]-2-ethoxy-N-(2-hydroxy-1-phenylethyl)propanamide (0.45 g, 0.84 mmol) obtained in example 21a in mixture of 1M sulphuric acid (17 mL) and dioxane/water (1:1, 39 mL) was heated at 90° C. for 88 h. The pH of the mixture was adjusted to 3.0 by addition of an aqueous sodium hydrogen carbonate solution. The mixture was extracted with ethyl acetate (2×25 mL) and the organic extract was washed with water (50 mL), brine (25 mL), dried (Na$_2$SO$_4$) and evaporated. The residue was chromatographed over silica gel using a gradient of 50–75% ethyl acetate in pet, ether to afford the title compound (0.2 g, 57%) as a white solid. mp: 77–78° C.

$[\alpha]_D^{25}$=+12.1 (c=1.0%, CHCl$_3$)

$^1$H NMR (CDCl$_3$, 200 MHz): δ 1.16 (t, J=7.0 Hz, 3H), 1.43–1.85 (bs, 1H, D$_2$O exchangeable), 2.86–3.14 (complex, 2H), 3.40–3.67 (complex, 2H), 3.90–4.08 (complex, 3H), 4.15 (t, J=6.65 Hz, 2H), 6.59–6.83 (complex, 10 H), 7.13 (d, J=8.4 Hz, 2H).

EXAMPLE 23

(−) 3-[4-[2-(phenoxazin-10-yl)ethoxy]phenyl]-2-ethoxypropanoic acid:

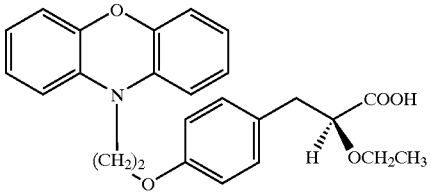

The title compound (0.19 g, 54%) was prepared as a white solid from diastereomer [(2S-N(1S)]-3-[4-[2-(phenoxazin-10-yl)ethoxy]phenyl]-2-ethoxy-N-(2-hydroxy-1-phenyl)ethylpropanamide (0.45 g, 0.84 mmol) obtained in example 21b by an analogous procedure to that described in example 22. mp: 89–90° C.

$[\alpha]_D^{25}$=−12.6 (c=1.0% CHCl$_3$)

$^1$H NMR (CDCl$_3$, 200 MHz): δ 1.16 (t, J=7.02 Hz, 3H), 1.42–1.91 (bs, 1H, D$_2$O exchangeable), 2.94–3.15 (complex, 2H), 3.40–3.65 (complex, 2H), 3.86–4.06 (complex, 3H), 4.15 (t, J=6.65 Hz, 2H), 6.63–6.83 (complex, 10H), 7.13 (d, J=8.54 Hz, 2H).

EXAMPLE 24

(±) 3-[4-(2-(Phenoxazin-10-yl)ethoxy]phenyl]-2-ethoxypropanoic acid, potassium salt:

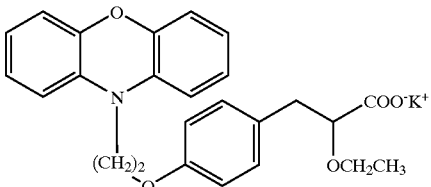

A mixture of (±) 3-[4-[2-(phenoxazin-10-yl)ethoxy] phenyl]-2-ethoxypropanoic acid (0.3 g, 0.72 mmol) obtained in example 15 and potassium tert. butoxide (88 mg, 0.72 mmol) in methanol (5 ml) was stirred at ca. 25° C. for 2h. The solvent was removed under reduced pressure and the residue was triturated with dry ether (3×3 mL). The supernatant solvent was decanted and further traces of ether was removed and dried under reduced pressure to afford the title compound (0.25 g, 76%) as a hygroscopic solid.

$^1$H NMR (CDCl$_3$, 200 MHz): δ 0.96–1.03 (t, J=6.82 Hz, 3H), 2.55–2.65 (m, 3H), 2.81–2.90 (m, 1H), 3.10–3.40 (t, J=7.05 Hz, 1H), 4.01–4.07 (t, J=5.30 Hz, 2H), 4.18–4.23 (t, J=5.30 Hz, 2H), 6.60–7.00 (m, 10 H), 7.1 (d, J=8.30 Hz, 2H).

EXAMPLE 25

(−) 3-[4-[2-(Phenoxazin-10-yl)ethoxy]phenyl]-2-ethoxypropanoic acid, magnesium salt:

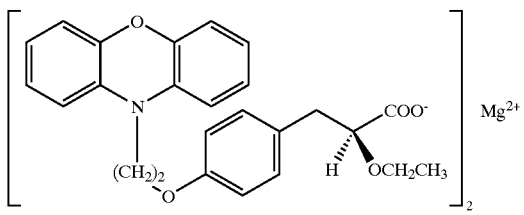

To a solution of (−) 3-[4-[2-(phenoxazin-10-yl)ethoxy]phenyl]-2-ethoxypropanoic acid (0.3 g, 0.72 mmol) obtained in example 23 in methanol (10 mL) was added magnesium hydroxide (20 mg, 0.345 mmol). The reaction mixture was stirred at room temperature ca. 25° C. for 72 h. The solvent was evaporated and the residue was triturated with diethyl ether and decanted to yield the title compound as a white solid (280 mg, 90%). mp: 300° C. (decomp).

$[\alpha]_D^{25}$=−31.0 (c=1.0%, CHCl3)

$^1$H NMR (CD$_3$OD, 200 MHz): δ 1.10 (t, J=7.00 Hz, 3H), 2.80 (dd, J=8.39Hz, 14Hz, 1H), 3.0 (dd, J=3.83 Hz, 1H), 3,20–3.40 (m, 1H), 3.50–3.70 (m, 1H), 3.80–3.90 (m, 1H), 3.99 (t, J=5.90 Hz, 2H), 4.20 (t, J=5.90 Hz, 2H), 6.54–6.90 (m, 6H), 7.16 (d, J=8.50 Hz, 2H).

EXAMPLE 26

(±) 3-[4-[2-(Phenothiazin-10-yl)ethoxy]phenyl]-2-ethoxypropanoic acid, arginine salt:

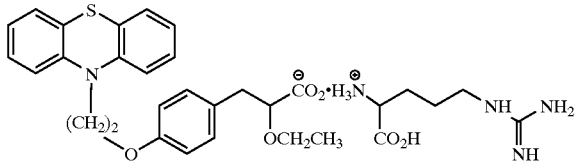

A mixture of (±) 3-[4-[2-(phenothiazin-10-yl)ethoxy]phenyl-2-ethoxypropanoic acid (50 mg, 0.115 mmol) obtained in example 11 and L-arginine (20 mg, 0.115 mmol) in methanol (3.0 mL) was stirred for 14 h at 30° C. Methanol was removed under reduced pressure and the residual mass was triturated with ether to afford the title compound as a white solid (62 mg, 88%). mp: 178° C.

$^1$H NMR (DMSO-d$_6$, 200 MHz): δ 1.08 (t, J=6.90 Hz, 3H), 1.72–1.84 (m, 4H), 2.86–2.90 (m, 2H), 3.16–3.30 (m, 4H), 3.52–3.56 (m, 2H), 3.68–3.91 (m, 2H), 4.28 (s, 4H), 6.70 (d, J=8.66 Hz, 2H), 6.74–6.96 (m, 2H), 7.00–7.23 (m, 8H).

EXAMPLE 27

(±) 3-[4-[2-(Phenoxazin-10-yl)ethoxy]phenyl]-2-ethoxypropanoic acid, arginine salt:

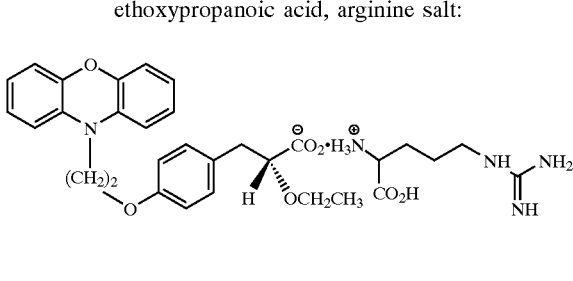

A solution of L-arginine (41.5 mg, 0.23 mmol) in water (0.25 mL) was added to a stirred solution of (+) 3-[4-[2-(phenoxazin-10-yl)ethoxy]phenyl-2-ethoxypropanoic acid (100 mg, 0.23 mmol) obtained in example 22 in ethanol (1 mL) at room temperature ca. 25° C. The reaction mixture was stirred vigorously for 16 h at the same temperature. The precipitated solid was filtered and dried under reduced pressure to yield the title compound (110 mg, 78%). mp: 196–198° C.

$[\alpha]_D^{25}$=+24.0 (c=0.5%, CHCl3)

$^1$H NMR (CD$_3$OD, 200 MHz): δ 1.04–1.11 (t, J=7.06 Hz, 3H), 1.71–1.87 (m, 4H), 2.78–2.90 (m, 2H), 3.18–3.26 (m, 3H), 3.54–3.58 (m, 2H), 3.75–3.85 (m, 1H), 3.96–4.01 (t, J=5.81 Hz, 2H, 4.17–4.23 (t, J=5.82 Hz, 2H), 6.60–6.82 (m, 10H), 7.15–7.19 (d, J=8.40 Hz, 2H).

EXAMPLE 28

(−) 3-[4-[2-(Phenoxazin-10-yl)ethoxy]phenyl]-2-ethoxypropanoic acid, arginine salt:

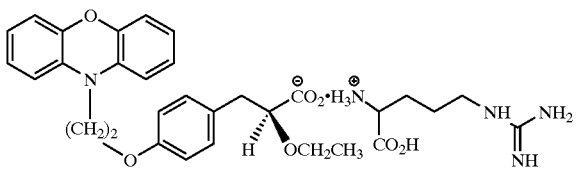

A mixture of (−)-3-[4-[2-(phenoxazin-10-yl)ethoxy]phenyl]-2-ethoxypropanoic acid obtained in example 23 (104.3 mg, 0.24 mmol) and L-arginine (43.3 mg, 0.25 mmol) in a mixture of ethanol (2.5 mL) and water (0.15 mL) was stirred for 24h at room temperature. The white precipitate formed was filtered and the solid was washed with dry ether (10–15 mL) to yield the title compound as a white solid (100 mg, 67.7%). mp: 145–147° C.

$[\alpha]_D^{25}$=−24 (C=0.545%, MeOH)

$^1$H NMR (DMSO-D6): δ 1.10 (t, J=7.06 Hz, 3H), 1.72–1.86 (m, 4H), 2.81–2.92 (m, 2H), 3.19–3.25 (m, 3H), 3.56–3.60 (m, 2H), 3.75–3.85 (m, 1H), 3.97–4.03 (t, J=5.72 Hz, 2H), 4.19–4.25 (t, J=5.82 Hz, 2H), 6.58–6.84 (m, 10H), 7.17–7.21 (d, J=8.27 Hz, 2H).

EXAMPLE 29

(−) 3-[4-[2-(Phenoxazin-10-yl)ethoxy]phenyl]-2-ethoxypropanoic acid, lysine salt:

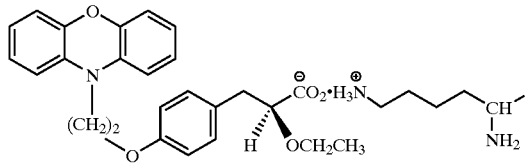

A mixture of (−) 3-[4-[2-(phenoxazin-10-yl)ethoxy]phenyl]-2-ethoxypropanoic acid (50 mg, 0.119 mmol) obtained in example 23 and lysine (17.5 mg, 0.119 mmol) in methanol (3.0 mL) was stirred for 36 h at room temperature ca. 25° C. under nitrogen atmosphere. Methanol was removed under reduced pressure and the residual mass was triturated with ether to afford the title compound as a white solid (65 mg, 96.4%), mp: 153–155° C.

$[\alpha]_D^{25}=-14.0$ (c=0.5% CHCl$_3$)

$^1$H NMR (CD$_3$OD, 200 MHz): δ 1.11 (t, J=7.01 Hz, 3H), 1.42–1.92 (m, 6H), 2.79 (q, J=7.05 Hz, 2H), 2.95 (dd, J=4.00, 12.6 Hz, 1H), 3.15–3.45 (m, 2H), 3.48–3.70 (m, 1H), 3.78 (dd, J=8.97, 4.00 Hz, 1H), 4.02 (t, J=5.80 Hz, 2H), 4.23 (t, J=5.85 Hz, 2H), 6.59–6.90 (m, 10H), 7.22 (d, J=8.73 Hz, 2H).

EXAMPLE 30

(±) 3-[4-[2-(Phenoxazin-10-yl)ethoxy]phenyl]-2-phenoxy-2-methylpropanoic acid, sodium salt:

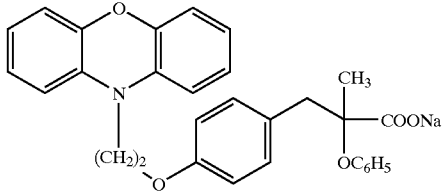

To a solution of (±) 3-[4-[2-(phenoxazin-10-yl)ethoxy]phenyl]-2-methyl-2-phenoxypropanoic acid (210 mg, 0.43 mmol) in dry methanol (4 mL) was added freshly prepared sodium methoxide (23 mg, 0.42 mmol) and allowed to stir the reaction mixture at 30° C. for about 2 h. Methanol was removed under reduced pressure and the residue was triturated with dry ether (3×5 mL) to afford the title compound as white hygroscopic solid (200 mg, 91%).

$^1$H NMR (DMSO, 200 MHz): δ 1.1 (s, 3H), 3.00–3.10 (dd, J=13.7 Hz, 2H), 3.90 (d, J=5.00 Hz, 2H), 4.18 (d, J=5.30 Hz, 2H), 6.60–6.90 (m, 8H), 7.10–7.30 (m, 4H).

EXAMPLE 31

(−) 3-[4-[2-(Phenothiazin-10-yl)ethoxy]phenyl]-2-ethoxy propanoic acid, arginine salt:

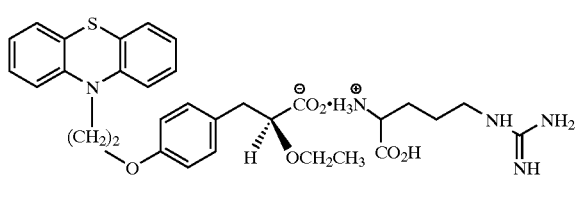

A mixture of (−) 3-[4-[2-(phenothiazin-10-yl)ethoxy]phenyl]-2-ethoxypropanoic acid (78 mg, 0.23 mmol) and L-arginine (34 mg, 0.23 mmol) in methanol (3 mL) was stirred for 14 h at 30° C. The solvent was removed and the residue was triturated with either or yield the title compound as white solid (70 mg, 64%), mp: 194° C.

$^1$H NMR (DMSO-D6): δ 1.08 (t, J=6.90 Hz, 3H), 3H), 1.73–1.84 (m, 4H), 2.83–2.90 (m, 2H), 3.15–3.31 (m, 4H), 3.53–3.55 (m, 2H), 3.70–3.90 (m, 2H), 4.28 (s, 4H), 6.79 (d, J=8,60 Hz, 2H), 6.76–6.98 (m, 2H), 7.01–7.21 (m, 8H).

EXAMPLE 32

(−) 3-[4-[2-(Phenothiazin-10-yl)ethoxy]phenyl]-2-ethoxypropanoic acid, lysine salt:

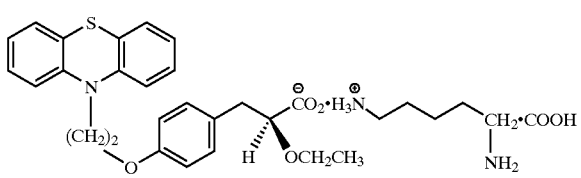

A mixture of (−)-3-[4-[2-(phenothiazin-10-yl)ethoxy]phenyl]-2-ethoxypropanoic acid (50 mg, 0.1079 mmol) and L-lysine (18 mg, 0.1079 mmol) in methanol (1 mL) was stirred for 14 h at room temperature. The solvent was removed and the residue was treated with dry ether (5 mL×2). The gummy mass was scratched when a pale solid separated from the ether layer. The ether layer was decanted to yield the title compound (55 mg, 85%). mp: 138–140° C.

$[\alpha]_D^{25}=-1.28$ (C=0.5%, MeOH)

$^1$H NMR (CDCl$_3$, 200 MHz): δ 1.07 (t, J=6.95 Hz, 3H), 1.51–1.89 (m, 4H), 2.87–2.94 (m, 2H), 3.29–3.30 (m, 5H), 3.50–3.53 (m, 2H), 3.71–3.80 (m, 1H), 4.28 (s, 4H), 6.76–6.80 (m, 2H), 6.92–6.95 (m, 2H), 7.01–7.21 (m, 8H).

EXAMPLE 33

(±) 3-[4-[2-Phenoxazin-10-yl)ethoxy]phenyl]-2-hydroxypropanoic acid, sodium salt:

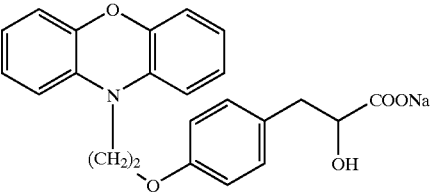

The title compound (80 mg, 47.33%) was prepared from (±) 3-[4-[2-(Phenoxazin-10-yl)ethoxy]phenyl]-2- hydroxypropanoic acid (160 mg, 0.49 mmol) obtained in example 17 by an analogous procedure to that described in example 12. mp: >280° C.

$^1$-H NMR ((DMSO-D6, 200 MHz): δ 2.88–2.96 (m, 2H), 4.01–4.404 (d, J=5.31 Hz, 2H), 4.15–4.18 (d, J=5.07 Hz, 2H), 6.60–6.90 (m, 10H), 7.10–7.20 (d, J=8.54 Hz, 2H).

EXAMPLE 34

(±) Methyl 3-[4-[2-(Phenoxazin-10-yl)ethoxy] phenyl]-2-phenoxypropanoate:

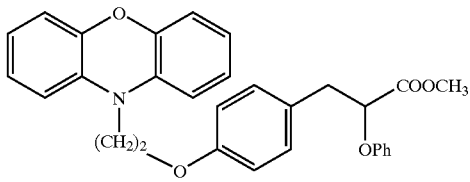

A solution of ethyl diethylphosphino phenoxy acetate in dry THF was added slowly to a stirred ice cooled suspension of sodium hydride in dry THF under nitrogen atmosphere. The mixture was stirred at 0° C. for 30 min. and added a solution of 4-[2-(Phenoxazin-10-yl)ethoxy]benzaldehyde in dry THF dropwise at ice temperature. The mixture was allowed to warm to room temperature and stirred for overnight. The solvent was evaporated under reduced pressure, residue was diluted with water and extracted with ethylacetated. The organic layer was washed with water, brine, dried and concentrated. The residue was chromatographed with 10% ethylacetate in pet, ether as an eluent to afford ethyl 3-[4-[2-(Phenoxazin-10-yl)ethoxy]phenyl]-2-phenoxypropanoate (59%) as thick liquid. Ethyl 3-[4-[2-(Phenoxazin-10-yl)ethoxy]phenyl]-2-phenoxypropanoate (3.5 gm) and magnesium turnings in dry methanol was stirred at room temp for 12 h. Methanol was evaporated and the residue was taken into water, acidified with 2N HCl and extracted with ethylacetate. The organic layer was washed with water, brine, evaporated and chromatographed with 10% ethylacetate in per. ether to yield the title compound (2.9 g, 85%). mp: 106–110° C.

$^1$H NMR ((CDCl$_3$, 200 MHz): δ 3.16–3.20 (d, J=6.23 Hz, 2H), 3.70 (s, 3H), 4.16 (m, 4H), 4.72–4.79 (t, J=6.32 Hz, 1H), 6.63–7.27 (m, 17H).

EXAMPLE 35

(±) 3-[4-[2-(Phenoxazin-10-yl)ethoxy]phenyl]-2-phenoxypropanoic acid:

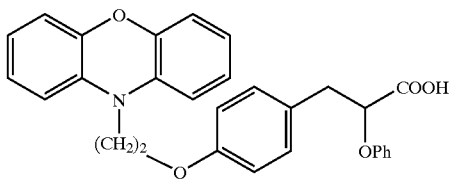

To a solution of (±) methyl 3-[4-[2-(Phenoxazin-10-yl) ethoxy]phenyl]-2-phenoxypropanoate (300 mg, 0.6 mmol) obtained in example 34 in methanol (15 mL) was added 10% NaOH solution (5 mL). The reaction was stirred at room temperature for 10 h. Methanol was removed and the residue was acidified with 2N HCl, extracted with ethylacetated (3×10 mL). The organic layer was washed with water, brine, dried and concentrated. The residue was chromatographed using 30% ethylacetate:pet, ether to afford a third liquid which was triturated with per ether to yield the title compound as a solid (192 mg, 66%). mp: 119–120° C.

$^1$H NMR (CDCl$_3$, 200 MHz): δ 3.23–3.26 (d, J=5.81 Hz, 2H), 3.94–4.00 (t, J=6.23 Hz, 2H), 4.14–4.20 (t, J=6.64 Hz, 2H), 4.81–4.87 (t, J=6.23 Hz, 1H), 6.61–6.89 (m, 12H), 6.96–7.04 (t, J=7.31 Hz, 1), 7.21–7.32. (m, 4H).

The compounds of the present invention lowered random blood sugar level, triglyceride, total cholesterol, LCL, VLDL and increased HDL. This was demonstrated by in vitro as well as in vivo animal experiments.

Demonstration of Efficacy of Compounds:

A) In vitro:

a) Determination of hPPARα activity:

Ligand binding domain of hPPARα was fused to DNA binding domain of Yeast transcription factor GAL4 in eucaryotic expression vector. Using superfect (Qiagen, Germany) as transfecting reagent HEK-293 cells were transfected with this plasmid and a reporter plasmid harboring the luciferase gene driven by a GAL4 specific promoter. Compound was added at different concentrations after 42 hrs of transfection and incubated overnight. Luciferase activity as a function of compound binding/activation capacity of PPARα was measured using Packard Luclite kit (Parkard, USA) in Top Count (Ivan Sadowski, Brendan Bell, Peter Broag and Melvyn Hollis. Gene. 1992, 118:137–141; Superfect Transfection Reagent Handbook, February, 1997. Qiagen, Germany).

b) Determination of hPPARγ activity:

Ligand binding domain of hPPARγ1 was fused to DNA binding domain of Yeast transcription factor GAL4 in eucaryotic expression vector. Using lipofectamine (Gibco BRL, USA) as transfecting reagent HEK-293 cells were transfected with this plasmid and a reporter plasmid harboring the luciferase gene driven by a GAL4 specific promoter. Compound was added at 1 μM concentration after 48 hrs of transfection and incubated overnight. Luciferase activity as a function of drug binding/activation capacity of PPARγ1 was measured using Packard Luclite kit (Packard, USA) in Packard Top Count (Ivan Sadowksi, Brendan Bell, Peter Broag and Melvyn Hollis. Gene. 1992. 118:137–141; Guide to Eukaryotic Transfections with Cationic Lipid Reagents. Life Technologies, GIBCO BRL, USA).

| Example No | Concentration | PPARα | Concentration | PPARγ |
|---|---|---|---|---|
| Example 11 | 50 μM | 6.42 Fold | 1 μM | 5.20 Fold |
| Example 15 | 50 μM | 3.30 Fold | 1 μM | 6.0 Fold |
| Example 28 | 50 μM | 9.5 Fold | 1 μM | 12.8 Fold |
| Example 29 | 50 μM | 6.0 Fold | 1 μM | 5.0 Fold |
| Example 30 | 50 μM | 9.3 Fold | 1 μM | 13.9 Fold | c) Determination of HMG CoA reductase inhibition activity:

Liver microsome bound reductase was prepared from 2% cholestyramine fed rats at mid-dark cycle. Spectrophotometric assays were carried out in 100 mM KH$_2$PO$_4$, 4 mM DTT, 0.2 mM NADPH, 0.3 mM HMG CoA and 125 μg of liver microsomal enzyme. Total reaction mixture volume was kept as 1 mL. Reaction was started by addition of HMB CoA. Reaction mixture was incubated at 37° C. for 30 min and decrease in absorbance at 340 nm was recorded. Reaction mixture without substrate was used as blank (Goldstein, J. L. and Brown, M. S. Progress in understanding the LDL receptor and HMG CoA reductase, two membrane proteins that regulate the plasma cholesterol, J. Lipid Res. 1984, 25: 1450–1461). The test compounds inhibited the HMG CoA reductase enzyme.

B) In vivo:

a) Efficacy in genetic models:

Mutation in colonies of laboratory animals and different sensitivities to dietary regimens have made the development of animal models with non-insulin dependent diabetes and hyperlipidemia associated with obesity and insulin resistance possible. Genetic models such as db/db and ob/ob (Diabetes, (1982) 31(1):1–6) mice and zucker fa/fa rats have been developed by the various laboratories for understanding the pathophysiology of disease and testing the efficacy of new antidiabetic compounds (Diabetes, (1983) 32: 830–838; Annu. Rep. Sankyo Res. Lab. (1994). 46:1–57). The homozygous animals, C57 BL/KsJ-db/db mice developed by Jackson Laboratory, US, are obese, hyperglycemic, hyperinsulinemic and insulin resistant (J. Clin. Invest., (1990) 85:962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Male C57BL/KsJ-db/db mice of 8 to 14 weeks age, having body weight range of 35 to 60 grams, bred at Dr. Reddy's Research Foundation (DRF) animal house, were used in the experiment. The mice were provided with standard feed (National Institute of Nutrition (NIN), Hyderabad, India) and acidified water, ad libitum. The animals having more than 350 mg/dl blood sugar were used for testing. The number of animals in each group was 4.

Test compounds were suspended on 0.25% carboxymethyl cellulose and administered to test group at a dose of 0.1 mg to 30 mg/kg through oral gavage daily for 6 days. The control group received vehicle (dose 10 mL/kg). On 6th day the blood samples were collected one hour after administration of test compounds/vehicle for assessing the biological activity.

The random blood sugar and triglyceride levels were measured by collecting blood (100 µl) through orbital sinus, using heparinised capillary in tubes containing EDTA which was centrifuged to obtain plasma. The plasma glucose and triglyceride levels were measured spectrometrically, by glucose oxide and glycerol-3-$PO_4$ oxidase/perioxidase enzyme (Dr. Reddy's Lab. Diagnostic Division Kits, Hyderabad, India) methods respectively.

The blood sugar and triglycerides lowering activities of the test compound was calculated according to the formula.

No adverse effects were observed for any of the mentioned compounds of invention in the above test.

| Compound | Dose (mg/kg) | Reduction in Blood Glucose Level (%) | Triglyceride Lowering (%) |
| --- | --- | --- | --- |
| Example 14 | 3 | 52 | 61 |
| Example 11 | 10 | 66 | 50 |
| Example 28 | 1 | 40 | 40 |
| Example 30 | 1 | 44 | 05 |

The ob/ob mice were obtained at 5 weeks of age from Bomboltgard, Demark and were used at 8 weeks of age. Zucker fa/fa fatty rats were obtained from IffaCredo, France at 10 weeks of age and were used at 13 weeks of age. The animals were maintained under 12 hour light and dark cycle at 25±1° C. Animals were given standard laboratory chow (NIN, Hyderabad, India) and water, ad libitum (Fujiwara, T., Yoshioka, S., Yoshioka, T., Ushiyama, I and Horikoshi, H. Characterization of new oral antidiabetic agent CS-045. Studies in KK and ob/ob mice and Zucker fatty rats. Diabetes. 1988. 37:1549–1558).

The test compounds were administered at 0.1 to 30 mg/kg/day dose for 9 days. The control animals received the vehicle (0.25% carboxymethylcellulose, dose 10 mL/kg) through oral gavage.

The blood samples wee collected in fed state 1 hour after drug administration on 0 and 9 day of treatment. The blood was collected from the retro-orbital sinus through heparinised capillary in EDTA containing tubes. After centrifugation, plasma sample was separated for triglyceride, glucose, free fatty acid, total cholesterol and insulin estimations. Measurements of plasma triglyceride, glucose, total cholesterol were done using commercial kits (Dr. Reddy's Laboratory, Diagnostic Division, India). The plasma free fatty acid was measured using a commercial kit form Boehringer Mannheim, Germany. The plasma insulin was measured using a RIA kit (BARC, India). The reduction of various parameters examined are calculated according to the formula.

In ob/ob mice oral glucose tolerance test was performed after 9 days treatment. Mice were fasted for 5 hrs and challenged with 3 gm/kg of glucose orally. The blood samples were collected at 0, 15, 30, 60 and 120 min for estimation of plasma glucose levels.

The experimental results from the db/db mice, ob/ob mice, Zucker fa/fa rats suggest that the novel compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

Blood glucose level and triglycerides are also lowered at doses greater than 0.10 mg/kg. Normally, the quantum of reduction is dose dependent and plateaus at certain dose.

b) Cholesterol lowering activity in hypercholesterolemic rat models:

Male Sprague Dawley rats (NIN stock) were bred in DRF animal house. Animals were maintained under 12 hour light and dark cycle at 25±1° C. Rats of 180–200 gram body weight range were used for the experiment. Animals were made hypercholesterolemic by feeding 2% cholesterol and 1% sodium cholate mixed with standard laboratory chow [National Institute of Nutrition (NIN), Hyderabad, India] for 6 days. Throughout the experimental period the animals were maintained on the same diet (Petit, D., Bonnefis, M. T., Rey, C and Infante, R. Effects of ciprofibrate on liver lipids and lipoprotein synthesis in normo- and hyperlipidermic rats. Atherosclerosis. 1988. 74: 215–225).

The test compounds were administered orally at a dose 0.1 to 30 mg/kg/day for 3 days. Control group was treated with vehicle alone (0.25% Carboxymethylcellulose; dose 10 mL/kg).

The blood samples were collected in fed state 1 hour after drug administration on 0 and 3 day of compound treatment. The blood was collected from the retro-orbital sinus through heparinised capillary in EDTA containing tubes. After centrifugation, plasma sample was separated for total cholesterol, HDL and triglyceride estimations. Measurement of plasma triglyceride, total cholesterol and HDL were done using commercial kits (Dr. Reddy's Laboratory, Diagnostic Division, India). LDL and VLDL cholesterol were calculated from the data obtained for total cholesterol, HDL and triglyceride. The reduction of various parameters examined are calculated according to the formula.

c) Plasma triglyceride and total cholesterol lowering activity in Swiss albino mice and Guinea pigs:

Male Swiss albino mice (SAM) and male Guinea pigs were obtained from NIN and housed in DRF animal house. All these animals were maintained under 12 hour light and dark cycle at 25±1° C. Animals were given standard laboratory chow (NIN, Hyderabad, India) and water, al libitum. SAM of 20–25 g body weight range and Guinea pigs of 500–700 g body weight range were used (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis. 1988. 70: 107–114).

The test compounds were administered orally to Swiss albino mice at 0.3 to 30 mg/kg/day dose for 6 days. Control mice were treated with vehicle (0.25% Carboxymethylcellulose; dose 10 mL/kg). The test compounds were administered orally to Guinea pigs at 0.3 to 30 mg/kg/day dose for 6 days. Control animals were treated with vehicle (0.25% Carboxymethylcellulose; dose 5 mL/kg).

The blood samples were collected in fed state 1 hour after drug administration on 0 and 6 day of treatment. The blood was collected from the retro-orbital sinus through heparinised capillary in EDTA containing tubes. After centrifugation, plasma sample was separated for triglyceride and total cholesterol (Wieland, O. Methods of Enzymatic analysis. Bergermeyer, H. O. Ed., 1963, 211–214; Trinder, P. Ann. Clin. Biochem. 1969, 6 : 24–27). Measurement of plasma triglyceride, total cholesterol and HDL were done using commercial kits (Dr. Reddy's Diagnostic Division, Hyderabad, India).

| Compound | Dose (mg/kg) | Triglyceride Lowering (%) |
|---|---|---|
| Example 28 | 1 mg | 22 |
| Example 30 | 1 mg | 58 |
| Example 25 | 1 mg | 6 |

Formulae for calculation:
1. Percent reduction in Blood sugar/triglycerides/total cholesterol were calculated according to the formula $$\text{Percent reduction (\%)} = \left[1 - \frac{TT/OT}{TC/OC}\right] \times 100$$

OC=Zero day control group value
OT=Zero day treated group value
TC=Test day control group value
TT=Test day treated group value 2. LDL and VLDL cholesterol levels were calculated according to the formula:

LDL cholesterol in mg/dl =

$$\left[\text{Total cholesterol} - \text{HDL cholesterol} - \frac{\text{Triglyceride}}{5}\right] \text{mg/dl}$$

VLDL cholesterol in mg/dl =

$$[\text{Total cholesterol} - \text{HDL cholesterol} - \text{LDL cholesterol}] \text{ mg/dl}$$

What is claimed is:
1. A compound of formula (Ih)

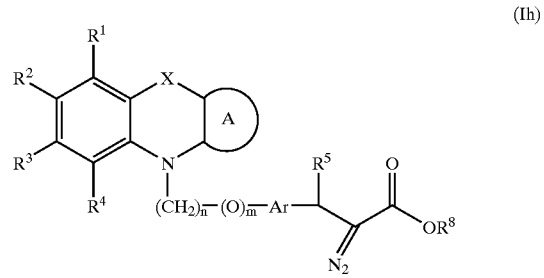

where $R^1$, $R^2$, $R^3$, and $R^4$ are the same or different and represent hydrogen, halogen, hydroxy, nitro, cyano, formyl or unsubstituted or substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; the ring A fused to the ring containing X and N represents a 5 or 6 membered cyclic structure containing carbon atoms, which optionally contains one or more heteroatoms selected from oxygen, sulfur or nitrogen atoms, which optionally may be substituted; the ring A is saturated or contains one or more double bonds or is an aromatic moiety; X represents a heteroatom selected from oxygen, sulfur or $NR^9$ where $R^9$ is hydrogen, alkyl, aryl, aralkyl, acyl, alkoxycarbonyl, aryloxycarbonyl or aralkoxycarbonyl groups; Ar represents an unsubstituted or substituted divalent single or fused aromatic or heterocyclic group; $R^5$ represents hydrogen atom, hydroxy, alkoxy, halogen, lower alkyl or unsubstituted or substituted aralkyl group or forms a bond together with the adjacent group $R^6$, $R^6$ represents hydrogen, hydroxy, alkoxy, halogen, lower alkyl group, acyl or unsubstituted or substituted aralkyl or $R^6$ forms a bond together with $R^5$; $R^8$ represents hydrogen or unsubstituted or substituted groups selected from alkyl, cycloalkyl, aryl, aralkyl, heteroaryl or heteroaralkyl groups; n is an integer ranging from 1–4 and m is an integer 0 or 1 or, polymorphs, tautomeric forms and stereoisomers thereof.

2. A compound according to claim 1 wherein the substituents on $R^1$–$R^4$ are selected from halogen, hydroxy, or nitro or unsubstituted or substituted groups selected from alkyl, cycloalkyl, alkoxy, cycloalkoxy, aryl, aryloxy, aralkyl, aralkoxy, alkoxyalkyl, aryloxyalkyl, aralkoxyalkyl, heterocyclyl, heteroaryl, heteroaralkyl, acyl, acyloxy, hydroxyalkyl, amino, acylamino, arylamino, aminoalkyl, alkoxycarbonyl, alkylamino, alkylthio, thioalkyl groups, carboxylic acid or its derivatives, or sulfonic acid or its derivatives.

3. A compound according to 1 wherein the cyclic structure A represents phenyl or pyridyl ring.

4. A compound according to 1 wherein Ar represents unsubstituted or substituted divalent phenylene, naphthylene, pyridyl, quinolinyl, benzofuryl, benzopyranyl, benzoxazolyl, benzothiazolyl, indolyl, indolinyl, azaindolyl, azainolinyl, indenyl, dihydrobenzofuryl, dihydrobenzopyranyl or pyrazolyl group.

5. A compound according to claim 4 wherein the substituents on the group represented by Ar are selected from linear or branched optionally halogenated $(C_1-C_6)$alkyl, optionally halogenated $(C_1-C_3)$alkoxy, halogen, acyl, amino, acylamino, thio, carboxylic acid and sulfonic acids and their derivatives.

6. A compound according to 1 wherein when m=0, Ar represents a divalent benzofuranyl, benzoxazolyl, benzothiazolyl, indolyl, indolinyl, dihydrobenzofuryl or dihydrobenzopyranyl group.

7. A compound according to 1 wherein when m=1, Ar presents divalent phenylene, naphthylene, pyridyl, quinolinyl, benzofurnyl, benzoxazolyl, benzothiazolyl, indolyl, indolinyl, azaindolyl, azaindolinyl, indenyl, dihydrobenzofuryl, benzopyranyl, dihydrobenzopyranyl or pyrazolyl groups.

8. A process for the preparation of compound of formula (Ih) defined in claim 1 which comprises a) reacting a compound of formula (IIIe)

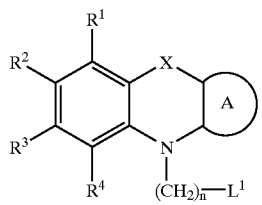

(IIIe)

where $L^1$ is a leaving group and all other symbols are as defined above with a compound of formula (Io)

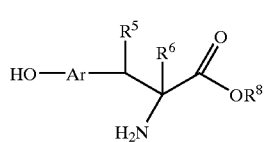

(Io)

where $R^6$ is hydrogen and all symbols are as defined above, to yield a compound of formula (In)

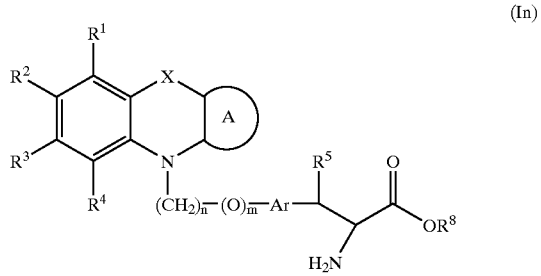

(In)

where all symbols are as defined above, and b) reacting a compound of formula (In) obtained above, with an appropriate diazotizing agent.

* * * * *